United States Patent
Rosengaus et al.

(10) Patent No.: US 7,072,034 B2
(45) Date of Patent: Jul. 4, 2006

(54) SYSTEMS AND METHODS FOR INSPECTION OF SPECIMEN SURFACES

(75) Inventors: Eliezer Rosengaus, Palo Alto, CA (US); Lydia Young, Palo Alto, CA (US)

(73) Assignee: KLA-Tencor Corporation, San Jose, CA (US)

( * ) Notice: Subject to any disclaimer, the term of this patent is extended or adjusted under 35 U.S.C. 154(b) by 370 days.

(21) Appl. No.: 09/965,408

(22) Filed: Sep. 25, 2001

(65) Prior Publication Data

US 2002/0186368 A1 Dec. 12, 2002

Related U.S. Application Data

(60) Provisional application No. 60/297,221, filed on Jun. 8, 2001.

(51) Int. Cl.
*G01N 21/88* (2006.01)

(52) U.S. Cl. .................................. 356/237.5

(58) Field of Classification Search ... 356/237.2–237.5
See application file for complete search history.

(56) References Cited

U.S. PATENT DOCUMENTS

| | | | |
|---|---|---|---|
| 4,247,203 A | 1/1981 | Levy et al. |
| 4,347,001 A | 8/1982 | Levy et al. |
| 4,378,159 A | 3/1983 | Galbraith |
| 4,391,524 A | 7/1983 | Steigmeier et al. |
| 4,441,124 A | 4/1984 | Heebner et al. |
| 4,448,532 A | 5/1984 | Joseph et al. |
| 4,532,650 A | 7/1985 | Wihl et al. |
| 4,555,798 A | 11/1985 | Broadbent, Jr. et al. |
| 4,556,317 A | 12/1985 | Sandland et al. |
| 4,579,455 A | 4/1986 | Levy et al. |
| 4,601,576 A | 7/1986 | Galbraith |
| 4,614,427 A | 9/1986 | Koizumi et al. |
| 4,618,938 A | 10/1986 | Sandland et al. |
| 4,633,504 A | 12/1986 | Wihl |
| 4,641,967 A | 2/1987 | Pecen |
| 4,644,172 A | 2/1987 | Sandland et al. |
| 4,766,324 A | 8/1988 | Saadat et al. |
| 4,805,123 A | 2/1989 | Specht et al. |
| 4,818,110 A | 4/1989 | Davidson |
| 4,845,558 A | 7/1989 | Tsai et al. |
| 4,877,326 A | 10/1989 | Chadwick et al. |

(Continued)

OTHER PUBLICATIONS

Patent Abstracts of Japan, publication No. 62276443, published Dec. 1, 1987.

(Continued)

*Primary Examiner*—Richard A. Rosenberger
(74) *Attorney, Agent, or Firm*—Ann Marie Mewherter; Daffer McDaniel, LLP

(57) ABSTRACT

Systems and methods for contact image sensor based inspection of specimens are provided. A system configured to inspect a specimen may include a contact image sensor. The contact image sensor may include a light source configured to direct light toward a surface of the specimen and a linear sensor array configured to detect light returned from the surface. The system may further include a processor configured to determine a presence of defects on the surface using the detected light. A method for inspecting the specimen may include directing light from a light source toward a surface of the specimen and detecting light returned from the surface using a linear sensor array. The light source and the linear sensor array may be arranged in a contact image sensor. The method may further include determining a presence of defects on the surface from the detected light.

75 Claims, 23 Drawing Sheets

U.S. PATENT DOCUMENTS

| | | | |
|---|---|---|---|
| 4,889,998 A | 12/1989 | Hayano et al. | |
| 4,898,471 A | 2/1990 | Vaught et al. | |
| 4,926,489 A | 5/1990 | Danielson et al. | |
| 5,076,692 A | 12/1991 | Neukermans et al. | |
| 5,096,291 A | 3/1992 | Scott | |
| 5,187,596 A | 2/1993 | Hwang | |
| 5,189,481 A | 2/1993 | Jann et al. | |
| 5,264,912 A | 11/1993 | Vaught et al. | |
| 5,274,434 A * | 12/1993 | Morioka et al. | 356/237.4 |
| 5,317,380 A | 5/1994 | Allemand | |
| 5,355,212 A | 10/1994 | Wells et al. | |
| 5,537,669 A | 7/1996 | Evans et al. | |
| 5,563,702 A | 10/1996 | Emery et al. | |
| 5,565,979 A | 10/1996 | Gross | |
| 5,572,598 A | 11/1996 | Wihl et al. | |
| 5,585,916 A * | 12/1996 | Miura et al. | 356/237.4 |
| 5,604,585 A | 2/1997 | Johnson et al. | |
| 5,737,072 A | 4/1998 | Emery et al. | |
| 5,798,829 A | 8/1998 | Vaez-Iravani | |
| 5,815,607 A | 9/1998 | Miura | |
| 5,822,055 A | 10/1998 | Tsai et al. | |
| 5,864,394 A | 1/1999 | Jordan, III et al. | |
| 5,883,710 A | 3/1999 | Nikoonahad et al. | |
| 5,917,588 A | 6/1999 | Addiego | |
| 6,020,957 A | 2/2000 | Rosengaus et al. | |
| 6,052,478 A | 4/2000 | Wihl et al. | |
| 6,064,517 A | 5/2000 | Chuang et al. | |
| 6,078,386 A | 6/2000 | Tsai et al. | |
| 6,081,325 A | 6/2000 | Leslie et al. | |
| 6,222,624 B1 * | 4/2001 | Yonezawa | 356/237.5 |
| 6,259,108 B1 * | 7/2001 | Antonelli et al. | 250/556 |
| 6,496,256 B1 * | 12/2002 | Eytan et al. | 356/237.5 |
| 6,791,680 B1 | 9/2004 | Rosengaus et al. | |

OTHER PUBLICATIONS

Patent Abstracts of Japan, publication No. 04332854, published Nov. 19, 1992.

Kitamura et al., "Automatic Macro Inspection System," SPIE vol. 3998, 2000, pp. 615-621.

"Contact image sensor heads," © ROHM Co., Ltd., 5 pages.

International Search Report, application No. PCT/US 02/02555, mailed Feb. 5, 2003.

* cited by examiner

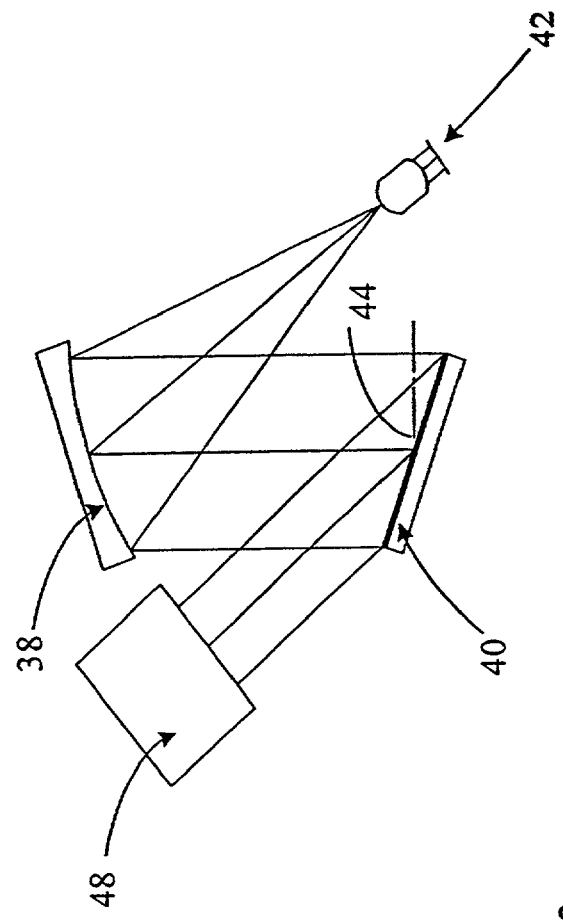
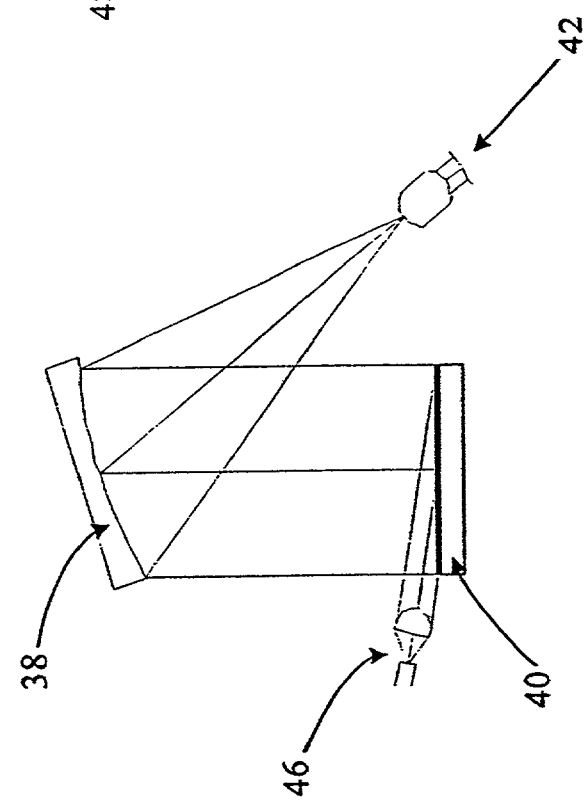
Fig. 3B
(Related Art)
Fig. 3A
(Related Art)

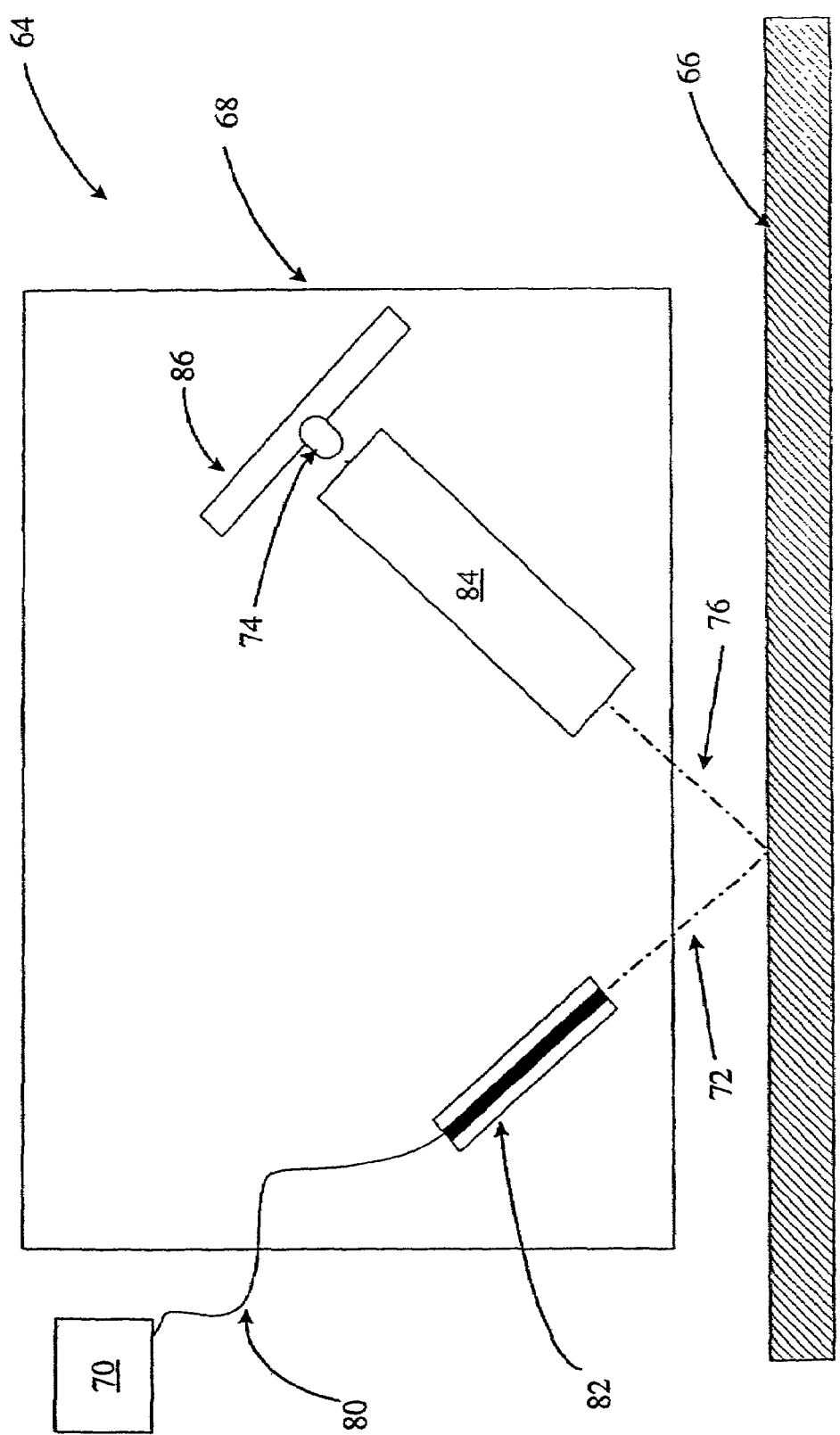

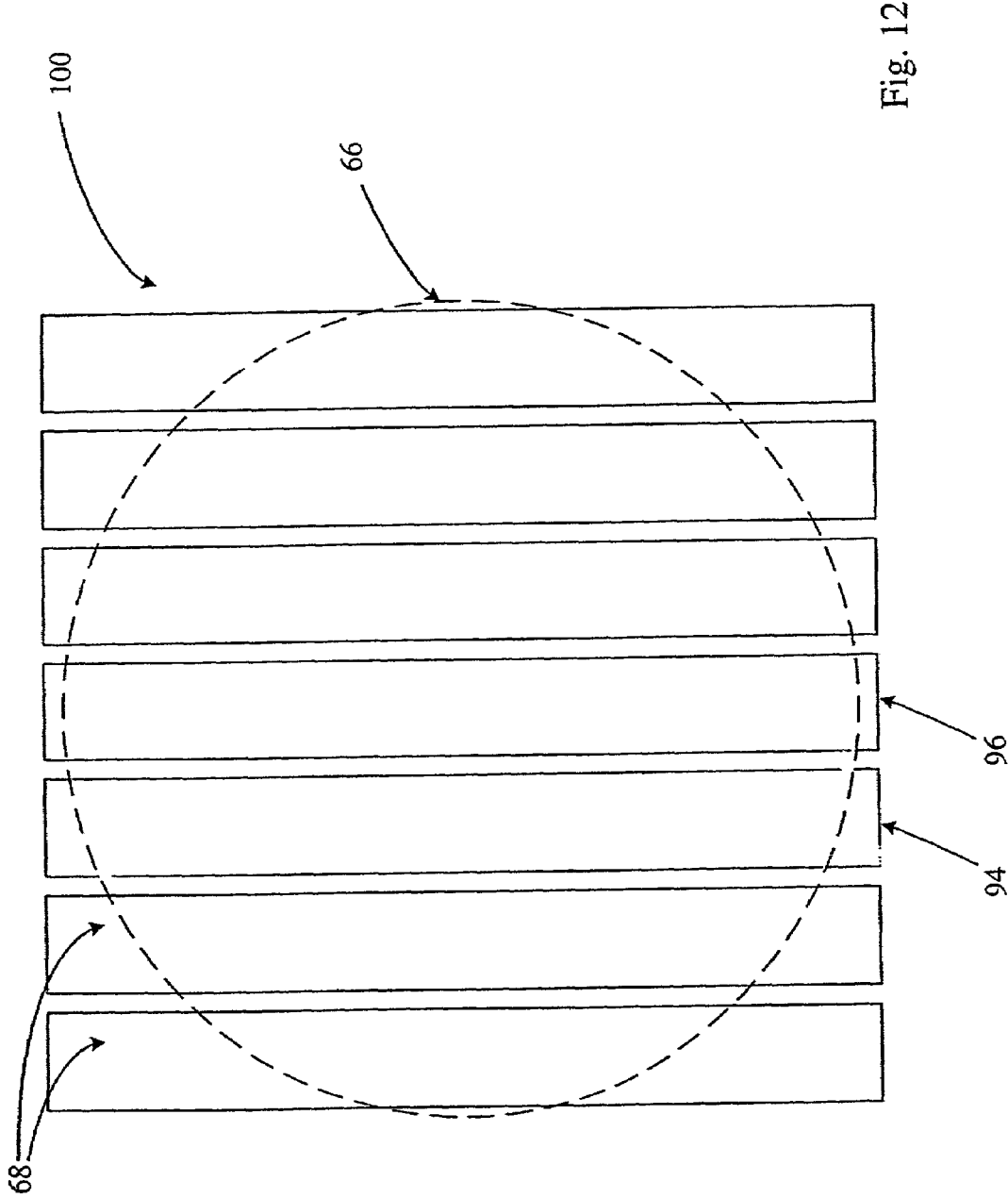

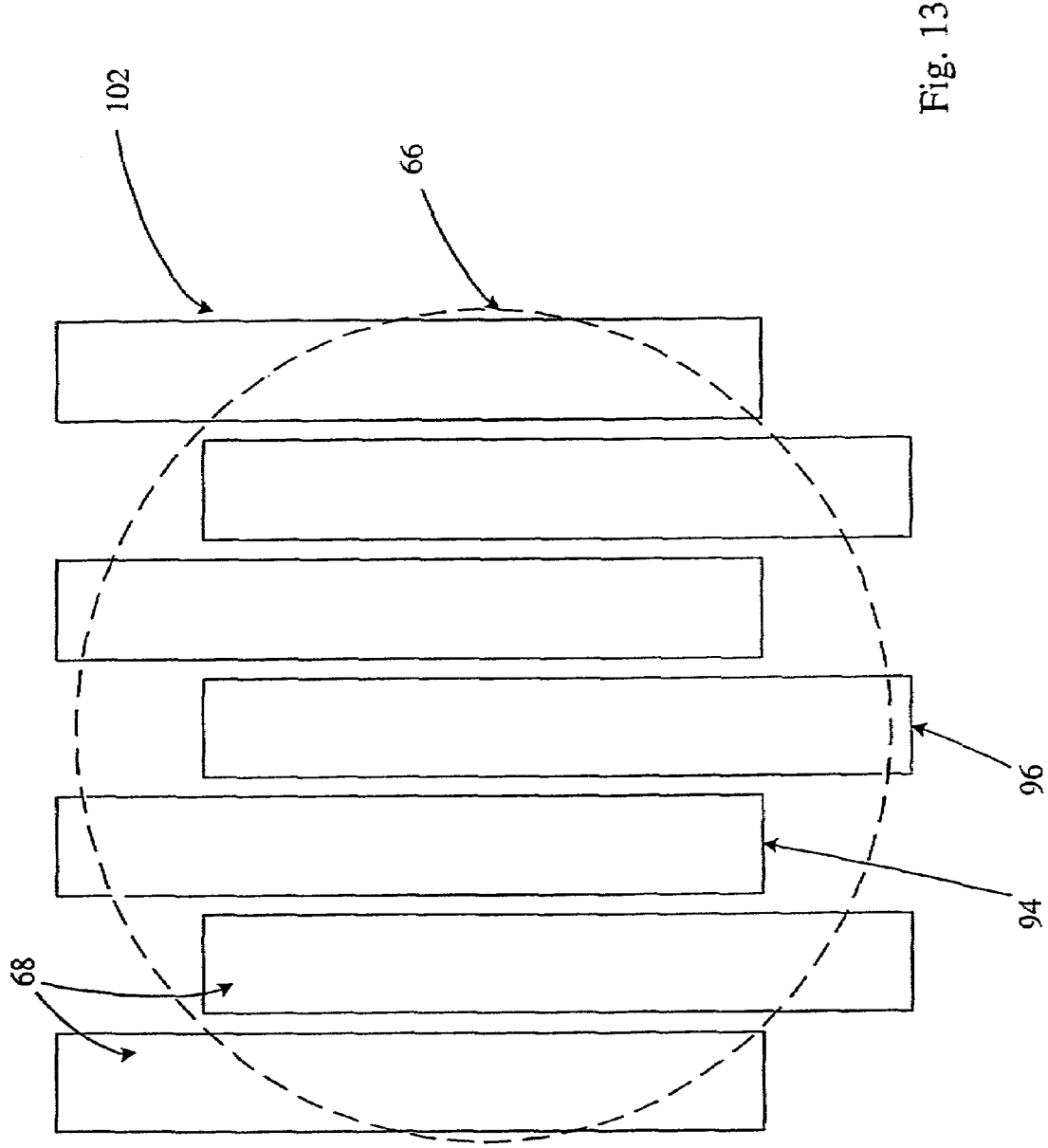

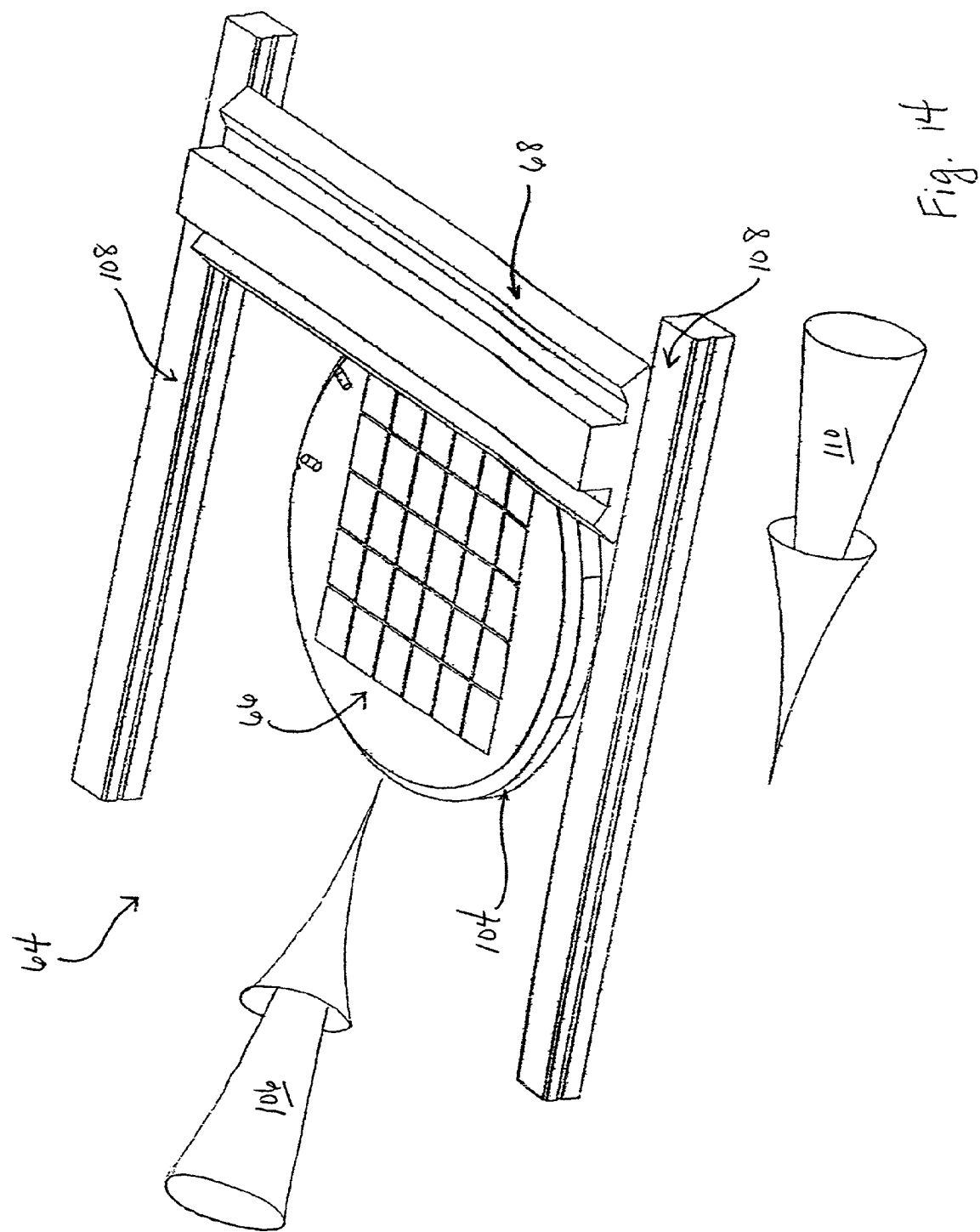

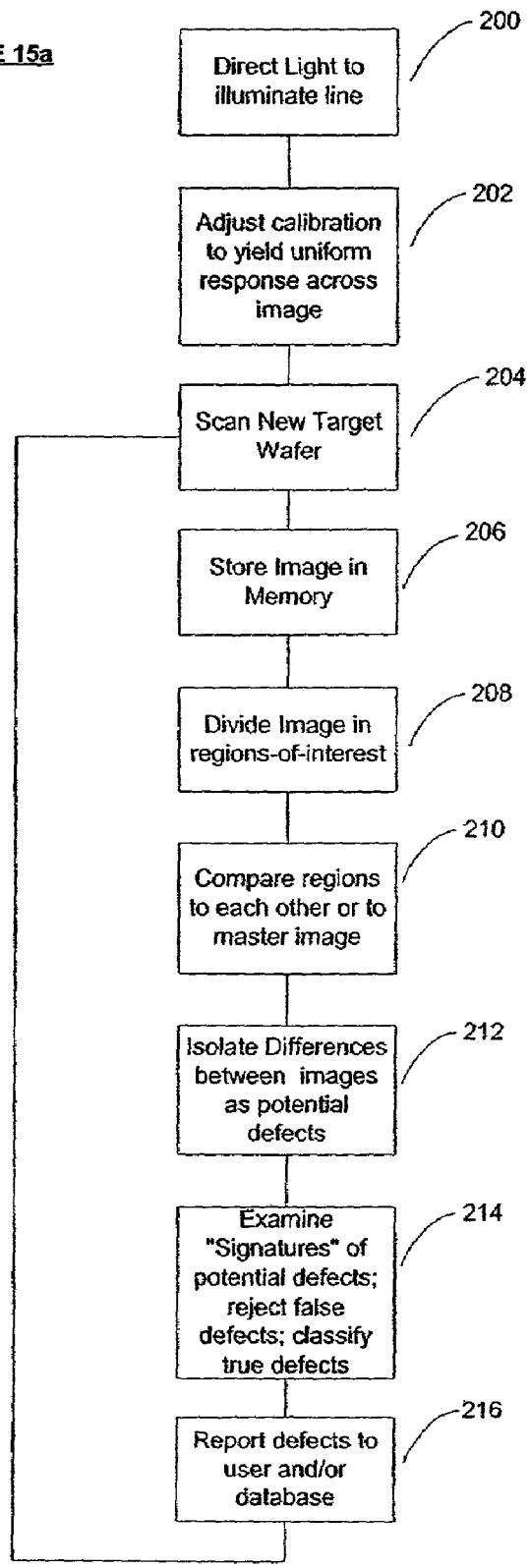

SYSTEMS AND METHODS FOR INSPECTION OF SPECIMEN SURFACES

This application claims the benefit of Provisional Application No. 60/297,221, filed Jun. 08, 2001.

BACKGROUND OF THE INVENTION

1. Field of the Invention

This invention generally relates to systems and methods for inspection of surfaces of specimens such as semiconductor wafers. Certain embodiments relate to systems and method for contact image sensor based detection of defects on such surfaces.

2. Description of the Related Art

Fabrication of semiconductor devices such as logic and memory devices includes using a number of processes to form various features and multiple levels or layers that comprise semiconductor devices on the surface of a semiconductor wafer, or similar substrate. For example, lithography is a semiconductor fabrication process that typically involves transferring a pattern to a resist on the surface of a semiconductor wafer. Additional examples of semiconductor fabrication processes may include chemicalmechanical polishing, etch, deposition, and ion implantation. Semiconductor devices are far smaller than the substrates, or wafers, and an array of multiple identical semiconductor devices is formed on the wafer, and then separated into individual semiconductor devices after all processing is completed.

During each semiconductor fabrication process, defects such as particulate contamination and pattern defects may be introduced into the semiconductor devices. Such defects may be found either randomly on a wafer surface, or may be repeated within each device found on the wafer. For example, randomly placed defects may be caused by events such as an unexpected increase in particulate contamination in a manufacturing environment or an unexpected increase in contamination in process chemicals that are used in fabrication. Defects that are repeated in each semiconductor device appearing on the entire wafer may, for example, be systematically caused by contamination or defects found on the reticle, or mask, that may then be transferred along with the desired device pattern during the lithography process.

As the dimensions of advanced semiconductor devices continue to shrink, the presence of defects in the semiconductor device limit the successful fabrication, or yield, of a semiconductor device. For example, a reticle defect that is reproduced in a patterned resist during lithography may cause an open circuit or a short circuit in a semiconductor device formed in subsequent processing. Because fabrication of a semiconductor device is composed of many complex process steps, the effects of defects on the total yield typically increase exponentially if an error that is caused by a defect is propagated throughout an entire semiconductor device. Thus, identifying and eliminating the sources of defects at critical steps during the fabrication process is an important objective to minimize cost. In particular, detection of defects at the appropriate process step may make possible rework or correction of the wafer as well as correction of any abnormal process deviations.

Defects commonly found during the after develop step in lithography are typically "macro" in size, ranging from about ten micrometers to the hundreds of millimeter dimensions of the whole wafer. Typically macro-level defects are those having lateral dimension greater than about 25 μm, but some macro-level defects such as scratches may have one dimension less than 25 μm and another well over 25 μm. The discussion herein primarily refer to the application of the inventive apparatus and methods in the field of after-develop inspection (ADI), though the applications for the invention and its methods are not intended to be limited to the ADI application.

The types of such macro or large-scale defects are quite varied, even within the class of lithography-related process steps. For example, one kind of defect type includes those resulting from resist or developer problems such as lifting resist, thin resist, extra photoresist coverage, incomplete or missing resist which may be caused by clogged dispense nozzles or an incorrect process sequence, and developer or water spots. Other examples of defects include regions of defocus caused by particles on the back side of a wafer ("hot spots"), reticle errors such as tilted reticles, out-of-focus exposure or incorrectly selected reticles, scratches, pattern integrity problems such as over or under developing of the resist, contamination such as particles or fibers, and non-uniform or incomplete edge bead removal ("EBR"). The term "hot spot" generally refers to a photoresist exposure defect that may be caused, for example, by a depth of focus limitation of an exposure tool, an exposure tool malfunction, a non-planar surface of the semiconductor topography at the time of exposure, foreign material on a back side of the semiconductor topography or on a surface of a supporting device, or a design constraint. With the exception of non-uniform or incomplete EBR, such defects generally occur randomly or systematically from lot-to-lot or from wafer-to-wafer. As such, macro-level defect inspection may involve inspecting all of the wafers in a lot or only a number of wafers in each lot.

These macro-level defects found on specimen surfaces particularly after the development of resist patterns placed during the lithography process are typically monitored manually by visual inspection, because many of these macro-level defects generated during a lithography process may be visible to the naked eye. Defects that may be visible to the human eye typically have a lateral dimension greater than or equal to approximately 100 μm. Defects having a lateral dimension as small as 10 μm, however, may also be visible on unpatterned regions of a wafer surface, or semiconductor topography. Prior to the commercial availability of automated defect inspection systems such as the systems illustrated in U.S. Pat. No. 5,917,588 to Addiego and U.S. Pat. No. 6,020,957 to Rosengaus et al., which are incorporated by reference as if fully set forth herein, manual inspection using an un-aided eye was the most common, and may still be the most dominant, inspection method used by lithography engineers.

The simplest method of manually inspecting a specimen surface is to tilt a hand-held specimen under a bright light, and look for the macro-level defects by an un-aided eye. Methods that are semiautomatic, but still rely on such visual inspection where an un-aided eye is used, may involve, for example, placing the wafer specimen on a semiautomatic tilt table and rotating the wafer through various angles under a bright light. The semiautomatic tilt table may rotate the wafer about a central axis while positioning the wafer at different inclinations relative to a plane normal to the central axis. In this manner, an operator can then visually inspect (i.e. with the unaided eye) the wafer surface for defects as it rotates, and then qualitatively evaluate if the wafer is acceptable or not for further processing. An example of a visual inspection method is illustrated in U.S. Pat. No. 5,096,291 to Scott and is incorporated by reference as if fully set forth herein.

There are, however, several limitations to applying visual inspection methods, where the un-aided eye is used. Typically such visual inspection methods are time-consuming and may be subject to operator error. In addition, lithography and automation trends in the semiconductor industry are recognizing macro-level defect inspection as a critical step to maintaining or enhancing yield, and are thus seeking methods that are more repeatable and reliable than human inspectors. Thus, many automated inspection systems such as described in the prior art by Addiego are being adopted for defect inspection to decrease the time required to inspect specimen surfaces and to increase the accuracy of the inspection process.

Inspection systems such as those described by Addiego use light scattering techniques that are typically comprised of an illumination system and a detection system. The illumination system illuminates a surface of a specimen such as a wafer with a source of light such as a laser or broadband lamp. Any defects that are present on the surface will scatter the incident light. The detection system is configured to collect the scattered light which can be converted into electrical signals which can be measured, counted, and displayed on an oscilloscope or other monitor. Examples of such inspection systems are illustrated in U.S. Pat. No. 4,391,524 to Steigmeier et al., U.S. Pat. No. 4,441,124 to Heebner et al., U.S. Pat. No. 4,614,427 to Koizumi et al., U.S. Pat. No. 4,889,998 to Hayano et al., and U.S. Pat. No. 5,317,380 to Allemand, all of which are incorporated by reference as if fully set forth herein.

In typical practice, however, the electrical signals are digitized to form an image of the scattered light. Further, the illumination area may be configured to be less than the specimen area, and then for fall coverage of the specimen, the specimen must move relative to the illumination source. Similarly, the detector may be configured to capture scattered light from an area less than the specimen area, and then for full coverage of the specimen, the specimen must move relative to the detection system. Typically, the illumination areas and detection areas are approximately equivalent in shape and size. There are three arrangements commonly used in inspection systems to collect images of whole specimens. An area well less than the dimensions of the specimen or wafer may be illuminated and imaged. By moving the specimen relative to the illuminator and detector in two dimensions, small area images may be collected, and a composite of the whole specimen may be formed by "stitching" or combining these small area images together. Alternatively, and as described by Addiego, an area with one dimension as larger or larger than the dimensions of the specimen and the other dimension well less than the dimensions of the specimen may be illuminated and imaged. By moving the specimen relative to the illuminator and detector in the direction substantially perpendicular to the long dimension of the illuminated area, a line scan image may be collected and then compiled into an image of the whole specimen. A third method illuminates the full specimen surface and collects a single image of the entire surface area of the specimen. In this case, the specimen may not need to move relative to the illumination and detection systems.

All three methods have been employed in prior art inspection systems. However, the prior art also is comprised of illumination and detection systems that use conventional optical systems composed of conventional lenses and detection sensors. For example, as shown in FIG. 1, a conventional optical system for a line scanning inspection system may include a conventional light source such as linear light source 10. In addition, a conventional lens may include lens 12 which may be configured to collect a line of scattered light rays 14 along a full length of a field of interest such as diameter 16 of specimen or wafer 18. Such a lens may be configured to direct the collected light rays 20 toward a camera that may include array 22 of charge-coupled device ("CCD") sensors. Often, conventional optical systems can be extremely expensive, may include very large optical components, and may have very large optical paths. Such disadvantages become increasingly important as the dimensions of the specimens increase. For example, the linear light sources in a line scanning system typically should have a length that is approximately as long as a diameter of the wafer specimen. Currently available macro-page defect line scanning systems employ linear light sources with demonstrated acceptable uniformity for specimens up to 200 mm wide. However, as the diameter of substrates increases to 300 mm and beyond, the length of such linear light sources must also increase proportionally to the increase in the diameter of the substrates. Such conventional light sources, however, may not have acceptable uniformities over such a larger length.

To ensure that defects can be discerned from effects that arise from illuminating the surface structures of the semiconductor devices being formed, the imaging optics must also be uniform across the specimen dimensions of interest. Specifically, the optimal imaging system should collect light at angles that are equivalent across the full surface area of interest. However, for the case of large specimen objects such as a 200 mm wafer, practical configurations of image collection optics that collect light with substantially the same collection angles across an entire surface often result in optical path dimensions that are quite large and components that are quite costly.

Using conventional optics, imaging all points equivalently may be addressed in a number of ways. For example, an imaging lens may be positioned very far away from a specimen surface. Placing the imaging lens very far away from the surface, however, may only minimize variations across the surface of interest and may result in poor light collection capabilities. Such an approach has several disadvantages such as a long optical path and difficulties associated with collecting sufficient light such that an acceptable throughput may be achieved. A long optical path may be addressed by using a number of mirrors that may fold an optical path with little loss or distortion of signal. Such an optical system, however, may dramatically increase the complexity of fabrication and alignment of the system.

Alternatively, as shown in FIG. 2, large diameter optical components comparable in size to the surface size of interest such as lens 24 or mirrors may be included in the optical assembly and may be positioned very close to specimen 26. For example, lens 24 may be spaced above the surface of the specimen 26 by height 28 typically of the order of tens of millimeters. Lens 24 may also be configured to collect a line of scattered light rays 30 across an entire field of interest such as diameter 32 of specimen 26. Such optical components may be arranged to collect light normal to a wafer surface of to result in a substantially telecentric optical system as shown by parallel scattered light rays 30. (A telecentric configuration is advantageous because it satisfies the requirement for uniformity in the imaging optics.) Establishing telecentricity using such a large diameter optical component, however, results in long optical path length 34 between lens and sensor array 36 typically of the order of hundreds of millimeters. Such large diameter optical components may be very expensive because the lenses need to be as large as the specimen. As shown in FIG. 2, a diameter of lens 24 must be greater than or equal to approximately a diameter of specimen 26 which may be approximately 300 mm. The cost of such a lens scales as approximately $d^4$, where d is the diameter of the specimen or wafer being imaged.

An example of a method for illuminating the entire surface area of a wafer is illustrated by Komatsu et al. in "Automatic Macro Inspection System," SPIE, Spring, 2000, which is incorporated by reference as if fully set forth herein. As shown in FIGS. 3A and 3B, such an inspection system includes large optical components such as mirror 38 which has a diameter approximately equal to a diameter of wafer 40. Mirror 38 is shown to be configured to direct and "fold" the light returned from a wafer surface 40 to sensor 42 which may be a CCD camera. For example, as shown in FIG. 3A, the wafer may be positioned with respect to the optical components such that scattered light may be directed by mirror 38 to sensor 42. Alternatively, as shown in FIG. 3B, the wafer may be positioned at tilting angle 44 with respect to the optical components such that diffracted light is directed by mirror 38 to sensor 42.

In addition, as shown in FIG. 3A, the prior art inspection system may also include long optical path lengths to provide uniform illumination from single point light source 46. A long optical path length of hundreds of millimeters is typically required to achieve telecentricity or near-telecentricity. Alternatively, as shown in FIG. 3B, such an inspection system may include diffuser 48 configured to create "full sky" illumination of an entire wafer surface area 40. Large optical components such as mirror 38 and diffuser 48, however, can be very expensive. Imaging a wafer can require a large field lens having a diameter approximately equal to the diameter of a wafer specimen.

Note that because conventional inspection systems typically have optical assemblies in which the illumination system and the detection system are separately mounted within the inspection system, often extensive calibration and preventive maintenance work are required to ensure that the systems are performing adequately.

As indicated previously, the semiconductor industry is increasingly moving towards fabrication of semiconductor devices on 300 mm semiconductor substrates to increase manufacturing yield and throughput. It is anticipated that processing of 300 mm semiconductor substrates will be fully automated or at least may require substantial mechanical handling of the substrates to minimize overall semiconductor device fabrication costs. For example, semiconductor fabrication facilities will likely include tracks configured to transport semiconductor substrates into and out of various fabrication tools. In this manner, clean room space for a tool is more efficiently utilized and costs of maintaining the clean room space can thus be minimized. Increased automation is desired to reduce human handling of the semiconductor substrates and the associated additional risks of contamination. In an automated fabrication line, continuous wafer flow is critical, and typically, flow rates are paced by the slowest module in the line. Typically, process tools have priority over inspection tools, and hence, the wafer flow in inspection tools must not impede overall wafer flow in the line. The wafer flow, or throughput, through an inspection tool must then be at least comparable to that of the process tools preceding it. Current state of the art lithography processing tools operate at >100 wafers per hour, and versions supporting 300 mm sized substrates are anticipated to run as high as 150 wafers per hour or more. All these adjustments being adopted for semiconductor fabrication of 300 mm wafers set changes or new requirements for the design of inspection tools. Inspection tools that have been developed for inspection of 200 mm semiconductor substrates may not be directly applicable in the semiconductor fabrication lines using 300 mm wafers, and thus may need to be completely, or at least significantly, redesigned to accommodate the new size and fabrication methodologies being introduced using 300 mm wafers.

The simplest approaches to designing inspection systems for inspection of 300 mm semiconductor substrates merely scale the technologies developed for inspection systems designed for 200 mm semiconductor substrates. However, several significant difficulties may arise in scaling current technologies. For example, maintaining low fabrication costs for imaging lenses that are larger and in proportion to the increased diameter of substrates and that maintain minimum distortion may be extremely difficult. Cost of optical elements increase rapidly with increases in a diameter (approximately on the order of $d^4$). An additional difficulty is ensuring equivalent or improved illumination uniformities for larger diameter substrates.

To support full automation to optimize processing flow and floor space usage, and to minimize errors introduced by human handling, thus minimizing overall cost, integrated process lines are anticipated for the fabrication of 300 mm-sized substrates. In this case, the inspection tools become part of the overall fabrication process line. Specifically, wafers might be transported directly from a process module directly and automatically into an inspection module through a track or using some other wafer handling device, and when the wafer has been inspected, it is removed from the inspection module and moved directly to the next process module using a wafer handling device. Currently, semiconductor fabrication process lines for substrates ≦200 mm in size contain some process and inspection tools that are integrated, and some that are stand-alone. In the case of the stand-alone tools, for example, a user must transport specimens from one process tool to the inspection tool, and then remove them and place them into the next process tool. Because some tools were intended to operate as stand-alone tools, these may have vertical and lateral dimensions that make integration into a semiconductor fabrication process line impractical. An inspection tool having smaller profile, but maintaining the inspection capabilities of stand-alone tools, may therefore have advantages attractive to integrated process lines.

To ensure that an inspection tool's throughput at least meets the semiconductor fabrication process line wafer flow requirements, the tool architecture for image capture and processing must be well optimized for time. The throughput of an inspection tool is paced by the time to load and unload wafers in the inspection module, the time to capture an image, and the time to analyze the image. An optimized inspection tool architecture may place image analysis in parallel with one of the other two key time components. Of these two remaining key time components, the time to capture an image is of most interest for this invention. Specifically, and as discussed above, image capture is a function of the illumination system and detection system of the inspection tool. Further, the time to capture an image is the time required to collect a sufficient amount of light scattered from the specimen surface, so that further processing of the digitized signal or image that results from the conversion of the collected light can discern the defects of interest. This collection time is also known as an exposure time, and specifically, is a function of the total amount of light provided to the specimen surface by the illumination system, the amount of light directed by the detection system optics, and the collection efficiency of the detection sensors. If, for example, the illumination source is very dim, then the amount of time required to collect sufficient light for an image that can discern the defects of interest may be very long. In the case of scaling conventional illumination system optics and conventional detection system optics to accommodate larger specimen sizes such as 300 mm wafers, delivery of sufficient light to the specimen surface and delivery of sufficient light to the detection sensors may become increasingly difficult without increase in the output of the illumination source itself. Specifically, illumination using the same illumination source power and scaled optics may result in reducing the illumination per area by at worst the square of the ratio of specimen size differences, and at best as the ratio of the specimen size differences, depending on the size and shape of the illumination area. For example, in scaling a full specimen illumination configuration from 200 mm diameter to 300 mm diameter, the total illumination per area may be reduced by $(100/150)^2$ or about 44%. For a line scan system, the reduction in illumination per area may be 200/300 or about 66%. In either of these cases, the exposure time may need to be increased to ensure that sufficient light is collected to provide an image that can discern the defects of interest. Increasing the exposure time results in decreasing the overall throughput. To compensate for the loss in illumination per area, the illumination source power may be increased. This may increase cost. Alternatively, the optical paths if conventional components are used may require re-design to increase delivery efficiencies. Increased costs and/or complexity may result.

SUMMARY OF THE INVENTION

Accordingly, it would be advantageous to develop an inspection method and system that is composed of elements that enable a pre-aligned optical assembly, telecentric illumination, minimum optical path lengths, minimum vertical and lateral dimensions such that the inspection system may be easily integrated into process tools to enable in situ inspection of specimens, high illumination delivery and collection efficiencies, and that provides all these features without loss with change in specimen size and without significant increase in cost.

There has been a need in other fields for imaging targets of sizes similar to those of a semiconductor wafer. Chief amongst them is document imaging for the purpose of facsimile transmission, electronic document storage or document copying. A common approach used in document scanners has been to use an imaging lens to create an image of a portion of the document (usually a line across it) onto an imaging sensor (usually a linear CCD device). This approach requires the use of a lens and a set of folding mirrors in order to minimize the size of the document scanner. Lately, document scanners have been redesigned to incorporate what is usually called a "Contact Image Sensor" or CIS, such as described in U.S. Pat. No. 5,187,596 of Hwang.

The concept of a CIS can be best illustrated by analogy as follows: a photographic copy of a negative is usually produced by imaging a target negative onto a sensor negative by using a lens to form the image. In this case, the size of the sensor and the image do not have to match. In fact, by selecting the distance from the imaging lens to the negative surfaces, a variable magnification can be introduced, whereby the photographic copy is either enlarged or reduced. Alternatively, a simpler and less expensive approach is to make a contact copy. In this approach, the target and sensor negatives are placed in close proximity, and light is projected through the source negative directly onto the target negative. In this approach, no lenses are used, and the vertical dimension of the copying apparatus is greatly reduced, since no space is required for the lens and the optical path from and to the lens. In the contact approach, a unity magnification is forced, i.e. the target (sensor) must be as large as the source.

Electronic approximations to the contact photographic printing approach are achieved in document scanners by using an array of rod lenses, each one imaging a very small portion of the target scanned line onto a sensor plane. This allows for a small working distance between the rod lenses and the source, which can be used to direct incident light onto the surface of the source, such light to be reflected by the source surface and directed by the array of rod lenses onto a line where a plurality electronic sensors are positioned adjacent to each other.

Commercially available contact image sensors are designed to image features of a document, whose imaging requirements are significantly different from those of semiconductor inspection tools. Specifically, document scanners have larger features, have no requirements to determine locations of features accurately, and have a comparatively narrow range of sample types to scan, which typically offer good contrast and reasonably isotropic light scattering/reflection so that illumination needs can be modest. The marginal image quality and limited resolution of commercially available contact image sensors may not be suitable for applications such as inspection of semiconductor specimens. Commercially available contact image sensors typically have a maximum resolution of approximately 600 dots per inch and more typically, a resolution of 300 dots per inch. This latter is approximately equivalent to a pixel size of approximately 85 µm, which is far larger than some of the defects of interest in the invention's application. Commercially available contact image sensors typically have light sources of limited intensity, a dynamic range of only approximately 9 bits, inaccurate positioning of the scan bar due to open loop positioning, and limited read speed of typical photosensors. Therefore, the limited performance capabilities of commercially available contact image sensors may prohibit using such sensors to inspect semiconductor topographies.

However, the technologies for contact image sensor configurations that meet the requirements for wafer inspection appear to be available. In particular, technologies are available that should result in significantly better imaging quality and resolution than commercially available sensors. For example, macro inspection requires approximately 20 µm pixel size, which is roughly equivalent to a resolution of about 1200 dots per inch, for which devices have been made. The use of illumination intensities high enough to image quasi-specular wafer surfaces requires different illuminators than those available in commercial contact image sensors. The electronic circuitry in commercial sensors can be replaced with low-noise, high-dynamic-range circuitry such that a dynamic range of greater than or equal to approximately 12 bits may be achieved. Technologies for positioning devices very accurately are well known (for example, such as those found in semiconductor lithography), and can be applied in this invention to position the contact image sensor with respect to the position of the wafer during inspection. Additionally, the contact image sensor may also be calibrated to correct for pixel gain variation and sensor distortion that may be caused by an assembly process for the sensor.

It is a purpose of this invention to use Contact Image Sensing technology to permit inspection of specimen surfaces (frontside and/or backside) and detection of macroscopic defects (defined as having lateral dimensions of on the order of tens of microns and above, up to the complete surface of a semiconductor wafer). It is a further purpose of the current invention to minimize the size of the inspection apparatus to permit integration of the apparatus into other semiconductor processing equipment. It is a further purpose of the current invention to minimize effects due to the optical geometry of the apparatus (e.g. lack of telecentricity).

BRIEF DESCRIPTION OF THE DRAWINGS

Other objects and advantages of the invention will become apparent upon reading the following detailed description and upon reference to the accompanying drawings in which:

FIG. 3A depicts a schematic side view of a related art system configured to image an entire surface area of a specimen in which the system includes a single point light source;

FIG. 3B depicts a schematic side view of a related art system configured to image an entire surface area of a specimen in which the system includes a diffuser;

FIG. 8 depicts a schematic side view of an embodiment of a system configured to inspect a specimen under bright field illumination;

FIG. 12 depicts a schematic top view of an embodiment of a substantially parallel arrangement of a plurality of contact image sensors;

FIG. 13 depicts a schematic top view of an embodiment of a staggered arrangement of a plurality of contact image sensors;

FIG. 14 depicts a schematic perspective view of an embodiment of a system configured to inspect a specimen;

FIG. 15a depicts a flow chart illustrating an embodiment of a method for inspecting a surface of a specimen;

Figure 1:
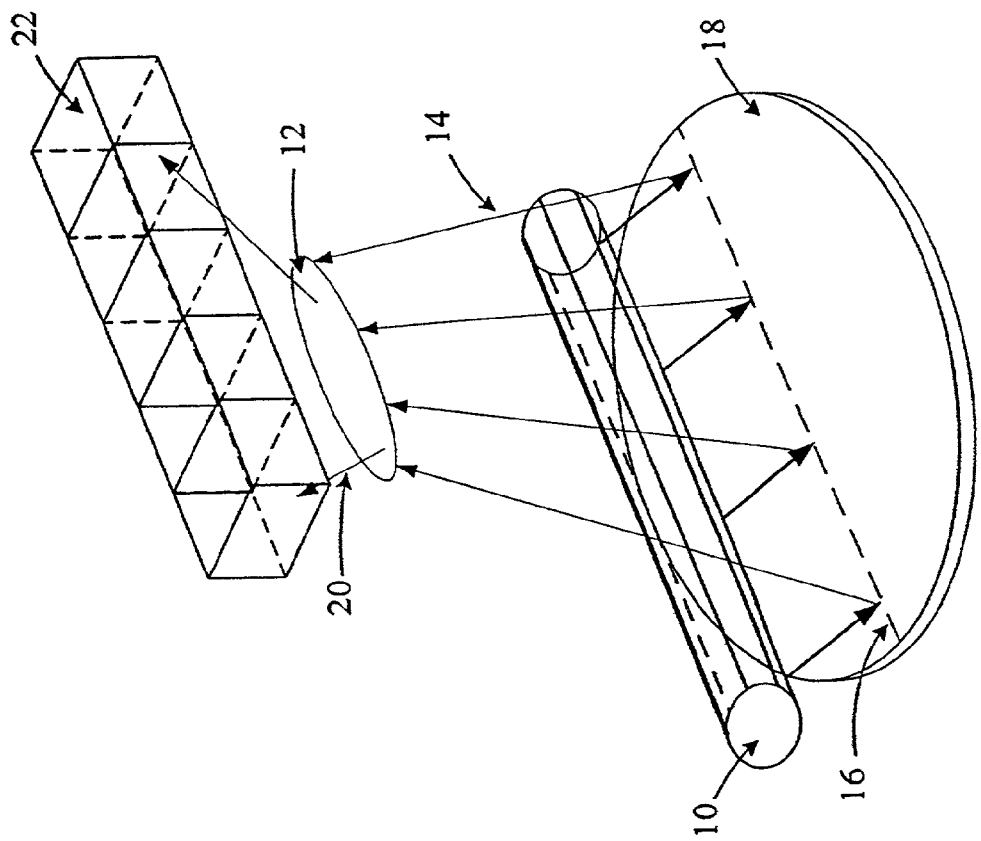
FIG. 1 depicts an isometric view of a related art system configured to image a specimen.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 4:
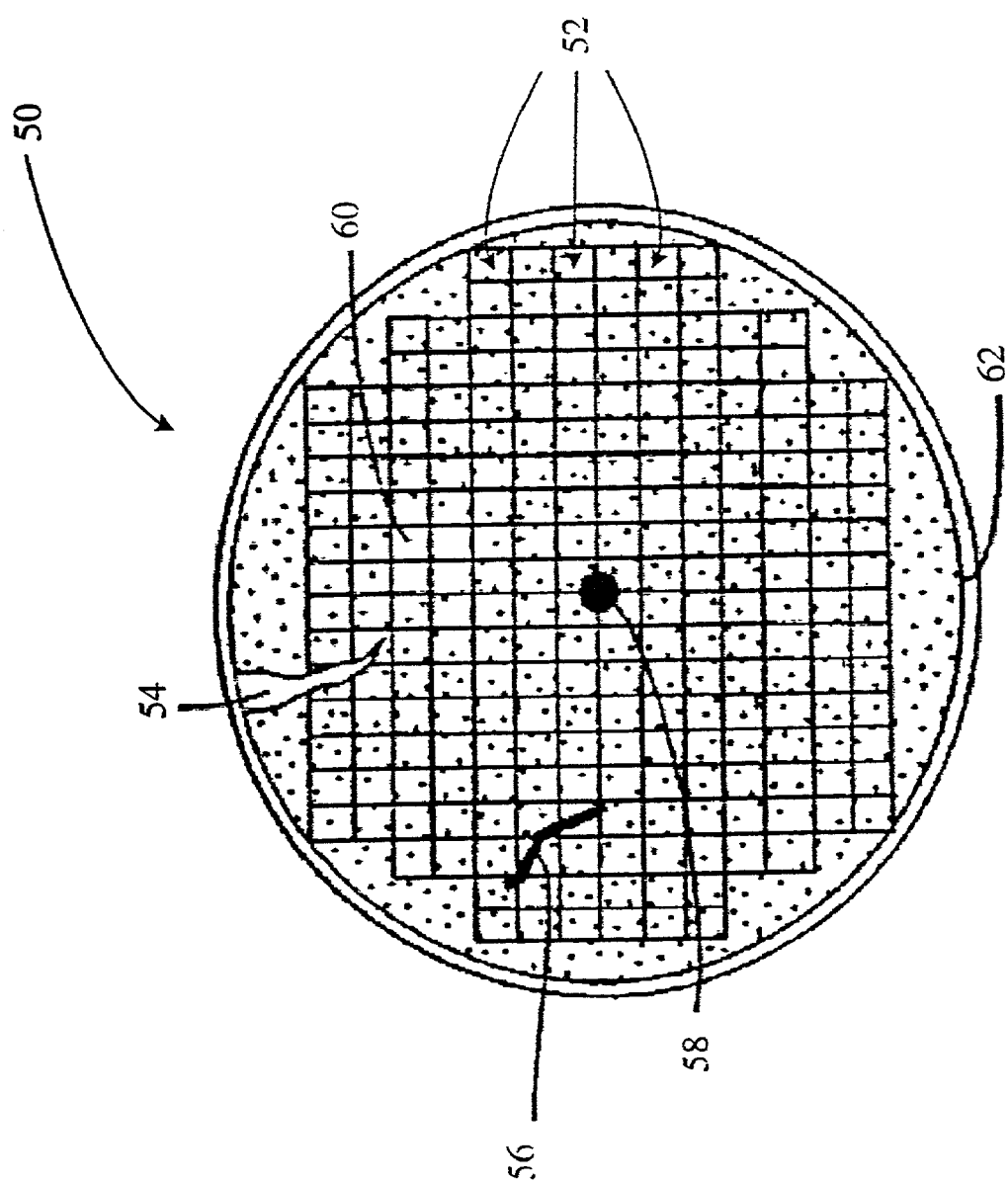
FIG. 4 depicts a schematic top view of an embodiment of a specimen having a plurality of defects on a surface of the specimen.

Turning now to the drawings, FIG. 4 illustrates a schematic top view of a specimen surface such as a semiconductor wafer 50 having a plurality of defects. Specimen or wafer 50 may include a plurality of dies 52 having repeatable pattern features. Alternatively, specimen 50 may be unpatterned such as a virgin wafer or a wafer prior to a first-pass lithography process. The class of specimens may include substrates typically found and/or processed in semiconductor fabrication factories. These specimens, or substrates, may be made of semiconductor or non-semiconductor materials, including but not limited to, monocrystalline silicon, silicon germanium, gallium arsenide, and glass materials such as quartz. Typically, the term "wafer" refers to substrates made of such semiconductor materials, and has also sometimes included substrates of non-semiconductor materials. The term "wafer" shall be used for these discussion purposes interchangeably with the term "specimen" though the inventive apparatus and methods can be applied more generically to the inspection of specimen surfaces.

Typically, specimen or wafer surface 50 may be comprised of one or more layers that may be formed on a semiconductor substrate. Such layers may include, but are not limited to, a resist, a dielectric material, a conductive material, and an epitaxial silicon layer. The resist may include photoresist materials that may be patterned by an optical lithography technique. Other resists, however, may also be used such as e-beam resists or X-ray resists which may be patterned by an e-beam or an X-ray lithography technique, respectively. Examples of an appropriate dielectric material may include, but are not limited to, silicon dioxide, silicon nitride, silicon oxynitride, and titanium nitride. Examples of an appropriate conductive material may include aluminum, polysilicon, and copper. The build-up and processing of these many layers of materials ultimately results in completed semiconductor devices. As such, specimen surface 50 may belong to a substrate that is in process of being completed (not all layers have been built), or that of a substrate with finished semiconductor devices.

Defect 54 on the specimen surface may be incomplete resist coverage, which may be caused by a malfunctioning coating tool or a malfunctioning resist dispense system. Defect 56 on the specimen surface 50 may be a surface scratch. Defect 58 on the specimen surface 50 may be a non-uniform region of a layer of resist that might be caused by a malfunctioning coating tool or a malfunctioning post apply bake tool. Defect 60 on the specimen surface 50 may be a "hot spot," as described in the Background. Foreign material on the back side of a wafer or on the surface of a supporting device may effectively deform the wafer. Such deformation of the wafer may cause a non-uniform focal surface during an exposure process. In addition, such a non-uniform focal surface may be manifested on the wafer as an unwanted or missing pattern feature change. Defect 62 on the specimen surface 50 may be non-uniform edge bead removal ("EBR"). Other common defects of interest for detection include lifting resist, developer or water spots, reticle errors such as errors caused by tilted reticles or incorrectly selected reticles, pattern integrity problems such as over or under developing of the resist, and contamination such as particles or fibers. Each of the defects described above may be present in any location on the specimen surface 50. In addition, any number of each of the defects may also be present on the surface. Defects may be found on the frontside and/or the backside of a specimen surface.

Some of the defects described above may be microscopic in nature (i.e, not visible by the bare human eye) and may require magnification optics. Others can be visible to the unaided eye and are considered "macroscopic" and range in size from approximately 10 μm to full wafer coverage. This invention focuses on detection of these macroscopic defects.

Different types of defects may be readily detected using different types of illumination. For example, each of the above described defects may have a characteristic signature under either dark field or bright field illumination. Scratches may appear as a bright line on a dark background under dark field illumination. Extra photoresist and incomplete photoresist coverage, however, may produce thin film interference effects under bright field illumination. In addition, large defocus defects may appear as a dim or bright pattern in comparison to a pattern produced by a laterally adjacent die under dark field illumination. Other defects such as defects caused by underexposure or overexposure of the resist, large line width variations, large particles, comets, striations, missing photoresist, underdeveloped or overdeveloped resist, and developer spots may have characteristic features under bright field and dark field illumination.

Figure 5:
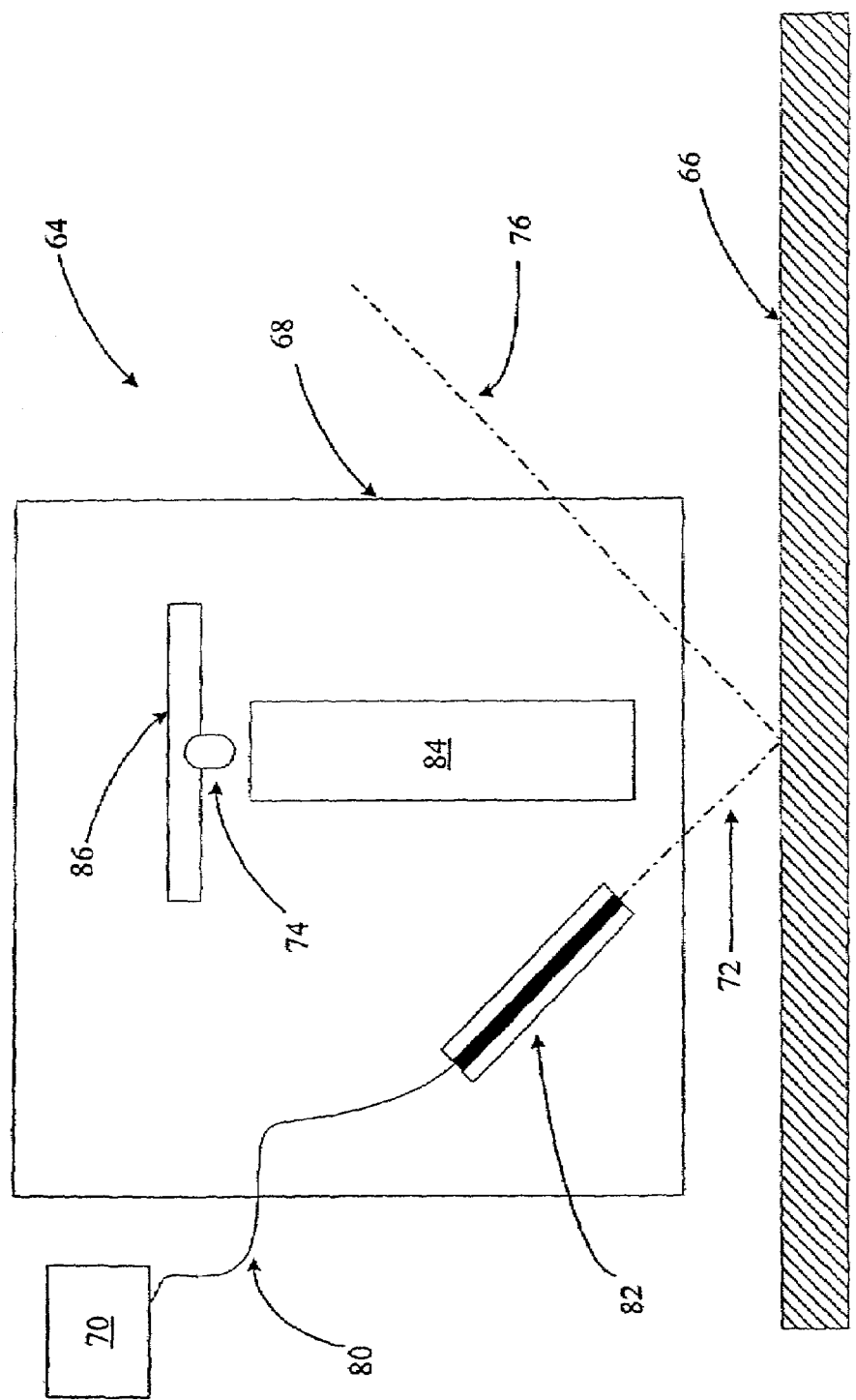
FIG. 5 depicts a schematic side view of an embodiment of a system configured to inspect a specimen under dark field illumination.
Figure 6:
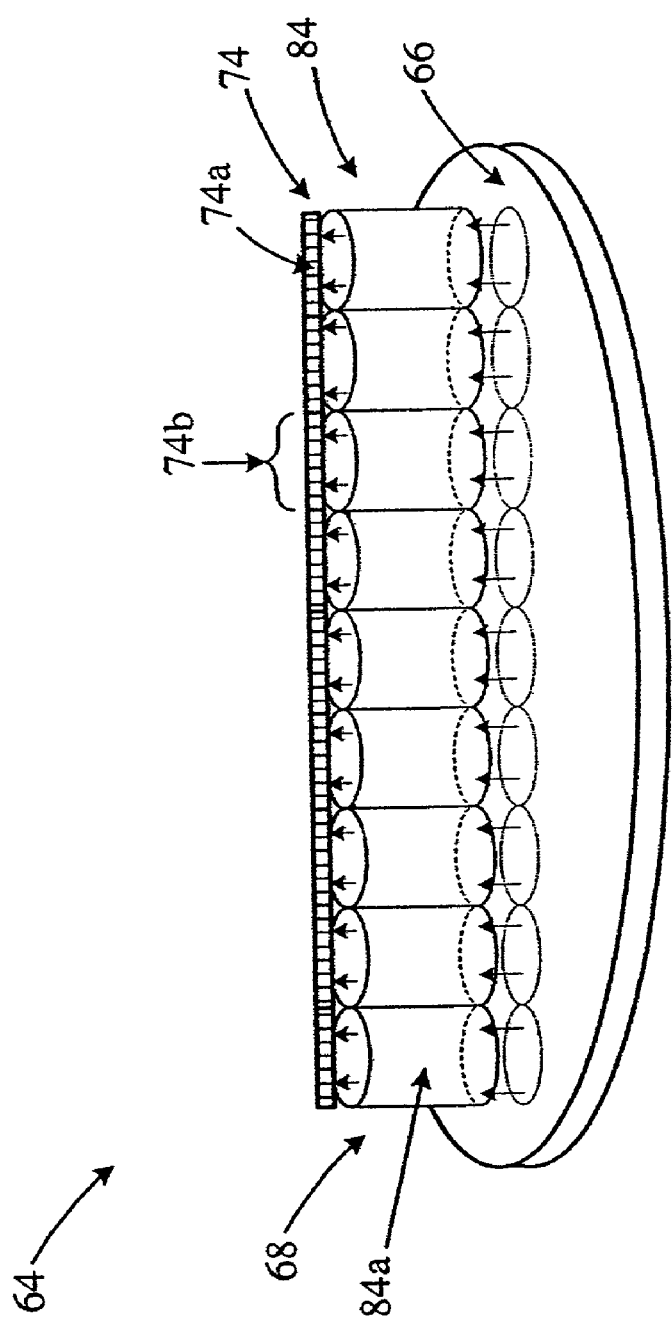
FIG. 6 depicts a schematic perspective view of an embodiment of a system configured to inspect a specimen under dark field illumination.
Figure 7:
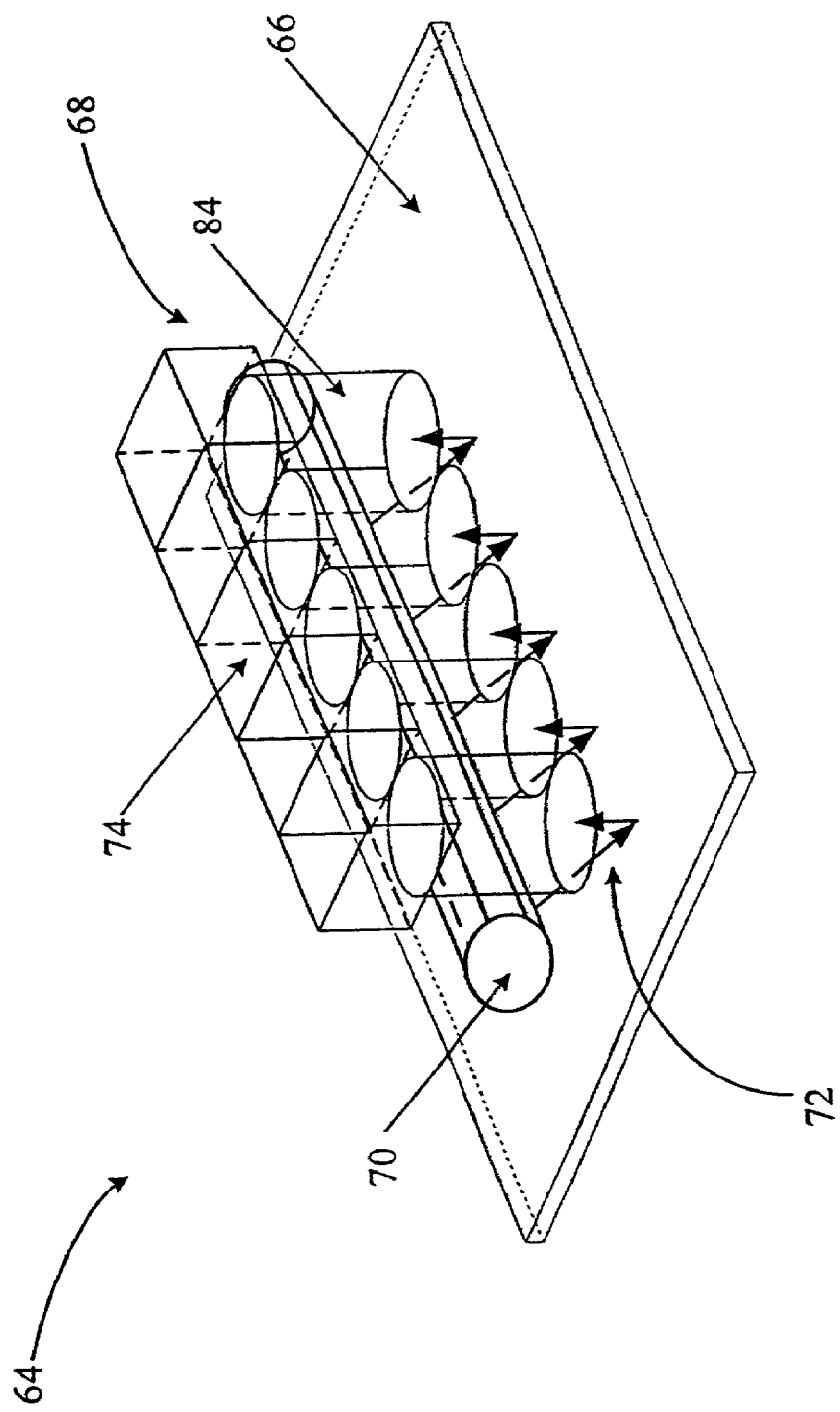
FIG. 7 depicts an isometric view of an embodiment of a system configured to inspect a specimen under dark field illumination.

FIGS. 5, 6 and 7 illustrate lateral cross sections and perspective views of one possible arrangement of the inventive system 64 configured to inspect wafer specimen 66 under dark field illumination. In this configuration, light reflected by a perfectly flat wafer 66 is directed away from the rod lenses 84 and is thus not captured. FIG. 7 illustrates an isometric view of system 64 configured to inspect wafer specimen 66 under dark field illumination. As will be further described herein, elements of inventive system 64 that are similarly configured in each of the embodiments illustrated in FIGS. 5–14 have been indicated by the same reference characters. For example, light source 70 may be similarly configured in each of the embodiments illustrated in FIGS. 5–14.

System 64 shows a contact image sensor-like device 68, which sits very close to the surface of interest and is configured for approximately unity magnification. Contact image sensor 68 typically can be located approximately 0.5 mm to approximately 20 mm, and more preferably approximately 3 mm to approximately 4 mm, from a specimen surface 66. Contact image sensor 68 is a device composed of an illumination system which delivers light to the surface of a specimen such as a wafer 66 and a detection system which collects the scattered light from the specimen surface and converts the light into usable electrical signals. Contact image sensor 68 as shown in FIGS. 5, 6 and 7 is a linear device, and as such, the illumination system and the detection system are also linear in their geometrical arrangements. Illumination system may include light source 70, and light delivery path comprised of elements 80 and 82 as will be described below. Detection system may include lens-like elements 84 and detection sensors 74, and the light collected by sensors 74 are converted to electrical signals through a circuit usually built on top of substrate 86. The various elements within the contact image sensor and the various configurations that may result are discussed in detail.

Figure 7A:
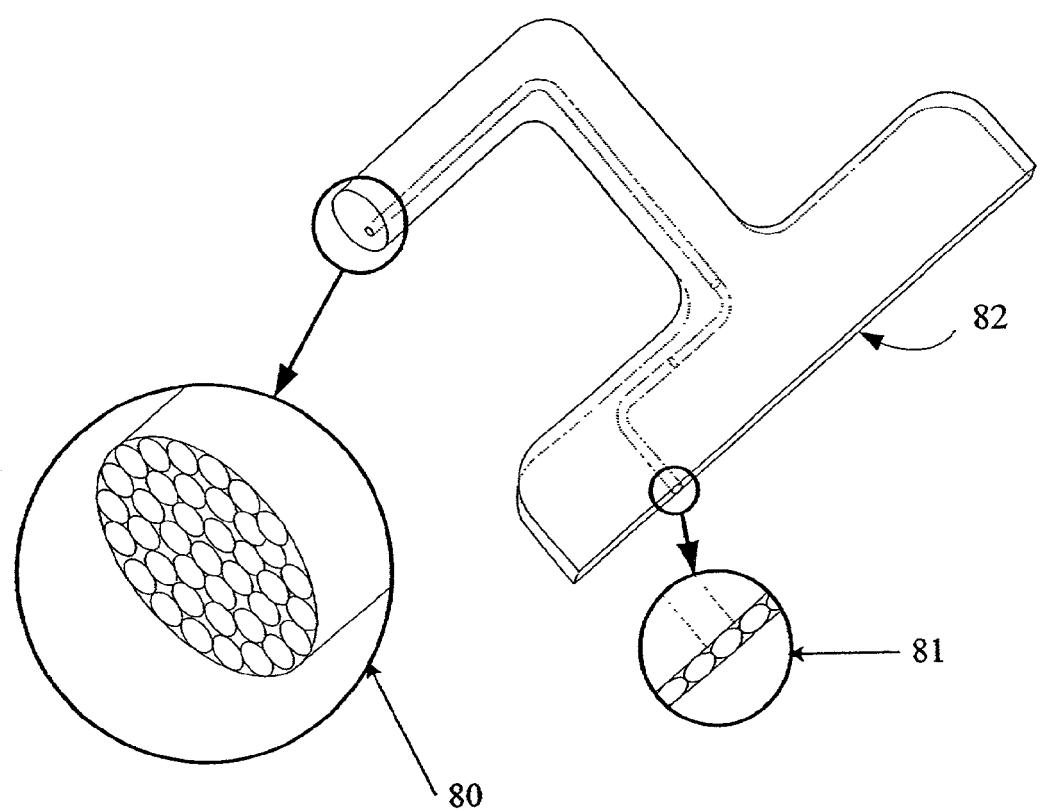
FIG. 7a depicts a schematic perspective view of an embodiment of a contact image sensor in which a fiber optic bundle is coupled to a fiber optic line source.

Light source 70 may reside within or outside the contact image sensor package. Light source 70 does not need to be linear in geometry. If, as shown by example in FIG. 5, light source 70 resides outside the contact image sensor, then a light delivery apparatus such as a fiber optic bundle 80 directs the light from light source 70 to the contact image sensor. Fiber optic bundle 80 does not need to be linear in geometry. Within the contact image sensor package is fiber optic line source 82, which is connected to fiber optic bundle 80. One way to transition from the bundle array 80 to the fiber optic line source 82 is to direct the bundle 80 to the contact image sensor and then spread and align the individual fibers into a linear shape and array, and transition to the fiber optic line source 82 having fibers along a line 81. This is illustrated in FIG. 7a.

Figure 7B:
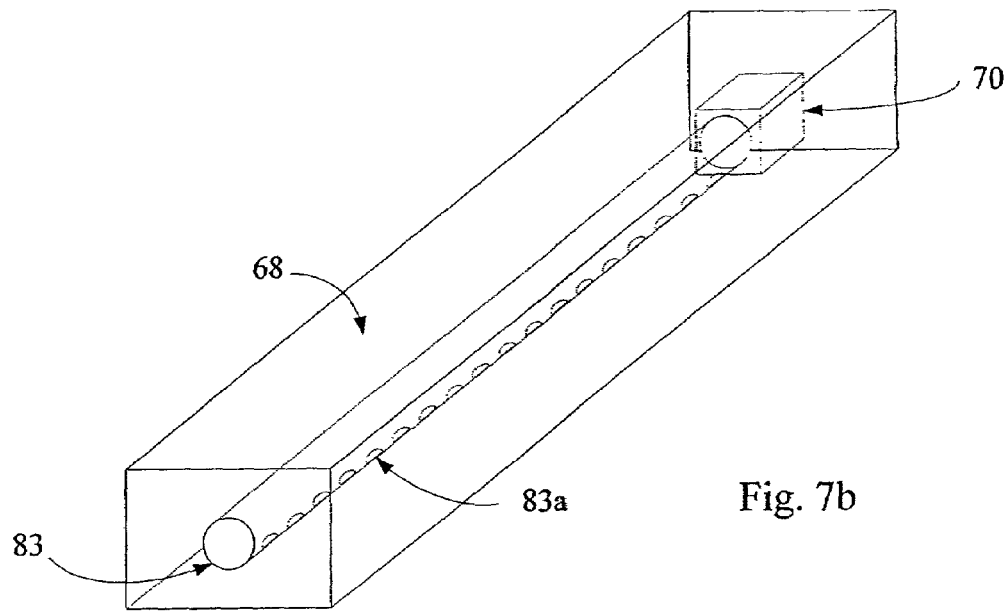
FIG. 7b depicts a schematic perspective view of an embodiment of a contact image sensor in which a light source is disposed within the contact image sensor.

If light source 70 resides within the contact image sensor package, it may feed directly into linear illumination source 82 (which may be an array of optical fibers). An example of how this may be arranged is shown in FIG. 7b. In this case, light source 70 is included positioned at one end of the contact image sensor assembly and a light-conducting rod, such as a light pipe, runs the length of the contact image sensor. The light pipe is made of material that enables substantially total internal reflectance along its length. The light pipe is configured to direct light out along one side of its length. For example, the light pipe may contain scattering apertures 83a, which are commonly referred to as "dimples," etched into the light pipe at varying intervals. The light conducted down the light pipe through internal reflectance may strike the apertures, then escape the light pipe and scatter thereby illuminating the specimen surface 66. In this manner, light is fed into the light pipe from light source 70, and the light pipe delivers light onto the specimen surface.

Figure 7C:
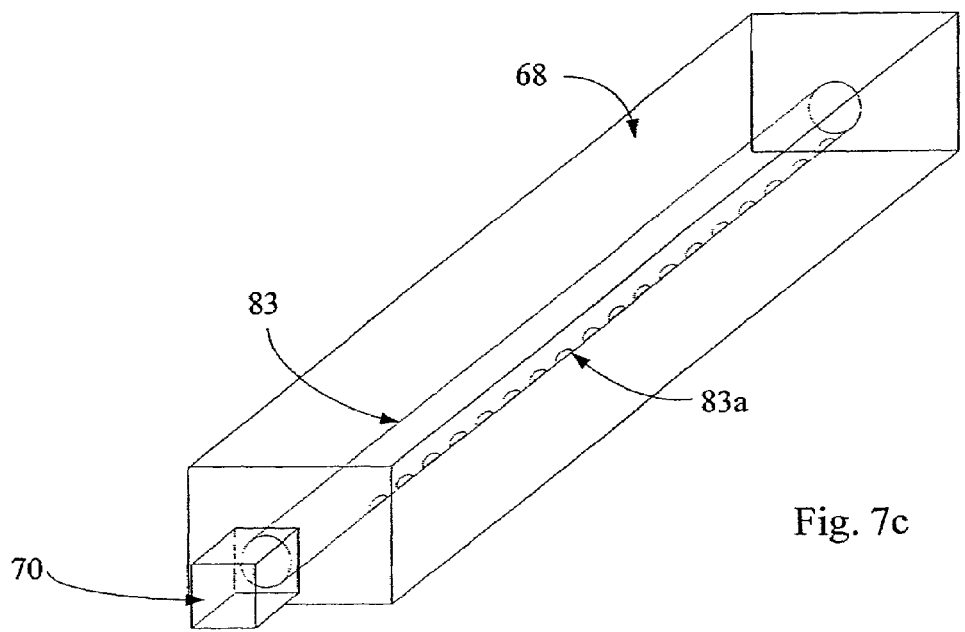
FIG. 7c depicts a schematic perspective view of an embodiment of a contact image sensor in which a light source is disposed external to the contact image sensor.

Alternatively, light source 70 may reside outside the contact image sensor package and feed a light pipe within the contact image sensor package via a fiber optic bundle 80 whose end abuts the light pipe end. See FIG. 7c.

Figure 7D:
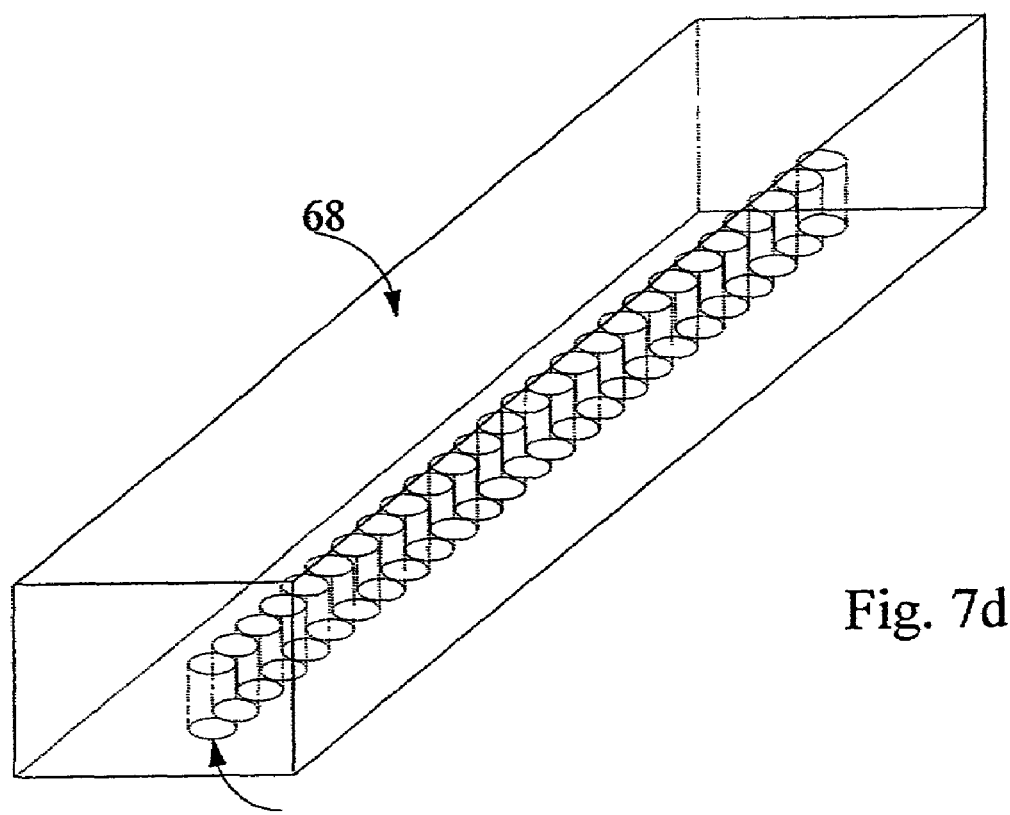
FIG. 7d depicts a schematic perspective view of an embodiment of a contact image sensor in which a fiber optic bundle is configured to direct light onto a surface of a specimen.

Alternatively, light source 82 may be a linear source extending the full length of the contact image sensor assembly and provide illumination directly onto the specimen surface. In this case, light source 70 and fiber delivery system 80 may be absent. See FIG. 7*d*. An example of a linear source may be composed of individual sources such as light emitting diodes that are butted together to form a linear array. Another example is a fluorescent tube of length greater than that of the sensor array.

Alternatively, light may be directed towards the wafer from a laser beam. The beam may be either fanned out to a line through the use of appropriate optics (such as cylindrical lenses, holograms, diffractive optics, etc. The beam may also be scanned at high speed by a galvanometer, resonant scanner, acousto-optic modulator or other device, in such a way as to synthesize a line by moving a laser beam spot across the wafer.

Yet another alternative is to use a conventional light source, such as an incandescent, high-intensity discharge or arc lamp, and shape the beam through the use of appropriate optics (such as mirrors, cylindrical lenses, etc.) into a line.

Thus, light source 70 may provide continuous or intermittent illumination of a specimen surface 66 either directly onto the surface, or through a light conducting path such as a fiber optic delivery system 80, 82. The light directed along path 72 from light source 70 through delivery system 80, 82 may strike the specimen surface at any in a range of angles of incidence with respect to the plane of the specimen surface 66. In FIG. 5, the angle of incidence is shown to be about 45 degrees. However, the angle of incidence or illumination may be different depending on the location of defects or features that may be present on specimen 66. For example, low angle illumination may be preferred when looking for defects on the specimen surface, while higher angles of incident illumination may be preferred for defects located in structures formed within the specimen. As such, the angle of incidence may range from approximately 5 degrees to approximately 85 degrees. In one embodiment, the angle of incidence may be varied by changing the angle of fiber optic bundle 82, relative to the plane of the wafer surface. Alternatively, the angle of incidence may be varied by changing the angular position of the row of apertures on a light pipe. Alternatively, additional optical components, such as mirrors or lenses, may be used to direct the light at a different angle of incidence.

The detection system of a contact image sensor assembly as shown by example in FIGS. 5, 6, and 7 collects the light scattered from the specimen surface 66. As previously indicated, the detection, or collection system, typically includes a light sensor assembly 74. Since the contact image sensor assembly is a linear geometric arrangement, the light sensor assembly 74 is usually a linear array of individual light sensors 74*a*. Typically, the light collected by the light sensor assembly 74 is converted into an electrical signal via a circuit often built directly onto substrate 86.

In an embodiment, each of the linearly aligned sensors may be paired with a dedicated light source in which the light source is arranged in a linear array of a plurality of light sources. In this manner, an arrangement of the plurality of light sources may correspond to an arrangement of the plurality of sensors.

In an additional embodiment, linear sensor array 74 may be assembled from shorter segments of light receiving portions 74*b* that is composed of individual sensors 74*a*, in a substantially straight line. The linear sensor array 74 may preferably be assembled in a process such that errors in the positioning of the light receiving portions 74*b* are avoided. In this manner, a substantially linear arrangement of sensors 74*a* may be obtained. Further, linear sensor array 74 may be assembled from shorter segments of light receiving portions 74*b* to form a length of at least one dimension such as a width or a diameter of a specimen. Thus, linear sensor array 74 may extend across the diameter or width of wafer specimen 66 such that when the contact image sensor 68 is scanned across the surface, all points along the diameter or width of the wafer specimen may be imaged. As such, the linear sensor array may be easily scaled to accommodate a plurality of wafer sizes. For example, the length of the linear sensor array 74 may be configured to be approximately 200 mm or approximately 300 mm.

Figure 2:
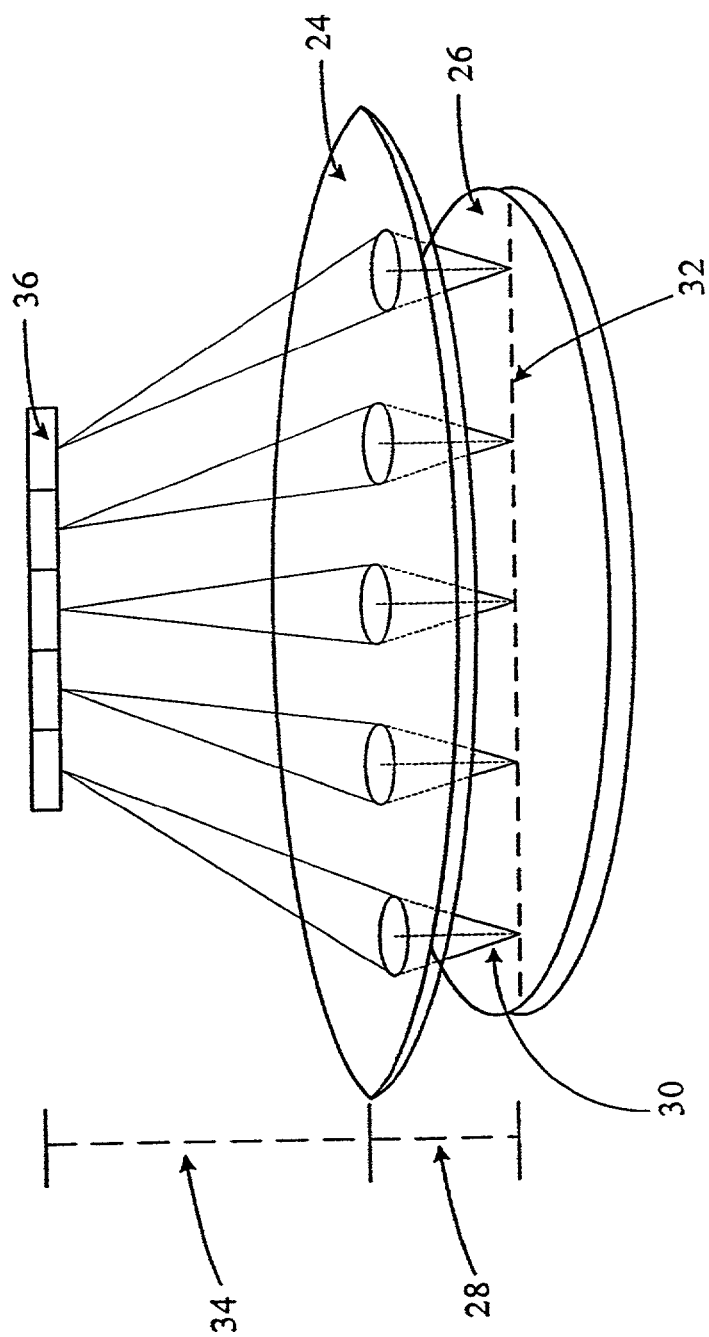
FIG. 2 depicts a schematic side view of a related art system configured to image a specimen in which the system includes substantially telecentric optics.

To help collect light returned from the specimen surface, the detection system of a contact image sensor assembly 68 may include a rod lens array 84 that is located in the scattered (FIG. 5) or reflected (FIG. 8) light path between the wafer surface 66 and the light sensor array 74. Since the contact image sensor is typically linear in geometry, the rod lens array is typically also a linear arrangement. FIGS. 6 and 7 illustrate a possible rod lens array configuration. Rod lens array 84 is commercially available under tradenames such as a "GRIN lens array" or a "SELFOC lens array." Rod lens array 84 is composed of a plurality of small diameter lenses. These lenses typically have a diameter on the order of 500 microns and length of a few millimeters. Each lens of rod lens array 84 forms a small image onto several sensors 74*a* of linear sensor array 74 as shown in FIGS. 6 and 7. In this manner, the rod lens array forms a "fly's eye" array, with a single lens dedicated to a small neighborhood of sensors. As such, each rod lens of the array may be configured to collect and direct light to only a few sensors of an array. In contrast and as discussed in the Background section and illustrated by example in FIGS. 1 and 2, conventional imagers may include a single lens which is configured to collect all of the light returned from a surface under inspection to a large array of individual sensors.

Each rod lens 84*a* of the rod lens array 84 may be configured to collect light returned from the specimen surface at substantially the same collection angle. Therefore, optical artifacts related to the position of the region being imaged with respect to the center of the wafer may be eliminated from the collected and detected light. As such, the contact image sensor provides substantially telecentric optical arrangement. Rod lens array 84 can have substantial light collection capabilities if the rod lens array is placed in close proximity to the specimen surface. For example, each rod lens 84*a* of the rod lens array 84 may have a numerical aperture of approximately 0.2 to approximately 0.7, and more preferably approximately 0.3 to approximately 0.5. In comparison, lenses that are used in inspection systems with conventional optics may have a numerical aperture of approximately 0.02. Light collection capability typically scales as the square of the numerical aperture. Therefore, such an array of rod lenses may provide light collection capabilities that may be approximately 625 times larger than the light collection capabilities of lenses in conventional inspection systems. Such light collection capabilities can provide significant advantages to a contact image sensor inspection system. For example, a wider variety of light sources including those having low intensity may be viable for use in such a system because the rod lenses collect a larger portion of the light returned from the specimen surface compared to lenses of conventional inspection systems. Alternatively, comparing the light collection capability of an inspection system using conventional optics to that of one using a contact image sensor assembly with both using the same light source 70, the system using the contact image sensor may have improved light collection capabilities. As such, the total exposure time may be reduced for the contact image sensor system because less time is required to collect the same amount of light as in the conventional optical system. As described in the Background section, shorter exposure time typically results in higher overall tool throughput. Alternatively, multiple illumination sources can be turned on and off in sequence before the sensor array moves substantially relative to the semiconductor wafer. These light sources may vary in wavelength, polarization, incident direction or degree of collimation. Analyzing the response of a particular signal to these different illumination methods may provide a "signature" to identify the signal as a defect or valid structure. Thus, multiple "channels" of information can be collected simultaneously during a single scan.

Contact image sensor 68 may also include circuit substrate 86 coupled to linear sensor array 74. Circuit substrate 86 may be made of a ceramic material or another material suitable to rigidly support the linear sensor array. Linear sensor array 74 may be further coupled to a wiring pattern on circuit substrate 86. Reflected or scattered and diffracted light detected by linear sensor array 74 may cause a charge on the each of the plurality of sensors. At pre-determined traversal intervals, a line clock formed on the circuit substrate may be triggered (preferably 300 to 1200 lines per inch), and the charge on the each of the plurality of sensors may be received by circuitry on circuit substrate 86. The circuitry may be designed to have output noise of only a few electrons such that a dynamic range of greater than or equal to approximately 12 bits. The charge may digitized by an analog/digital converter (not shown) coupled to circuit substrate 86 and the digital data may be sent through an interface to an image processing device (not shown) coupled to contact image sensor 68 in system 64. For example, the digital data may be sent to a memory medium of a host computer or a personal computer.

The role of the image processing device is to process the image data from the contact image sensor assembly 68 and determine whether defects are present, and what kinds of defects these images represent. Image processing for the purposes of inspection of surfaces or other entities is well known to those practiced in the art. Additional examples of data processing of detected light are illustrated in U.S. Pat. No. 5,917,588 to Addiego, the complete disclosure of which is hereby incorporated by reference.

Thus, the primary elements of a contact image sensor assembly 68 have been described and include an illumination system composed of a light source 70 and a light delivery system composed of all or in part elements 80 and 82, and a detection system composed of a sensor array 74, a rod lens array 84, and associated electronics 86. These same elements are similar but not equal to those found in a conventional inspection system. Some of the differences have already been described, such as the capabilities of the rod lens array as compared to a conventional imaging lens. Other differences that are advantageous for a contact image sensor based system are further described below.

One key difference between the contact image sensor assembly 68 and conventional optical system is size. Specifically, the optical components of contact image sensor assembly 68 such as light delivery system 80 and 82, rod lens array 84, and linear sensor array 74 may have extremely compact geometries and thus may be disposed such that the optical paths are very short. Hence, contact image sensor 68 can be quite small. For example, contact image sensor 68 may have a height of less than approximately 30 mm, and more preferably less than approximately 10 mm, yielding a contact image sensor inspection system with an extremely low profile. With rod lens array 84 coupled to linear sensor array 74, the rod lens array may be positioned within a few millimeters of the specimen surface. For example, the rod lens array may be disposed within the contact image sensor and placed above the specimen surface 66 by less than approximately 10 mm, and more preferably by less than approximately 3 mm. The rod lens array itself is only a few millimeters in height, and the sensor array may be positioned to butting or near butting against the rod lenses. Hence, the optical path between the specimen surface 66 and the sensor array is approximately the same as the rod lens length, or no more than a few millimeters. This is in comparison to the optical paths of tens or hundreds of millimeters as described by FIGS. 1 and 2 and in the Background section. Finally, commercially available sensor arrays also have thickness of a few millimeters, and thus, an overall package height of the contact image sensor of a approximately 10 mm is possible. In a preferred embodiment, the rod lenses 84*a* are approximately 500 microns in diameter, and are disposed in an array maintained generally parallel to a surface of a 300 mm semiconductor wafer during inspection, with a separation between the lenses and the wafer surface of approximately 2 to 3 microns. In this preferred embodiment, the rod lenses 84*a* are approximately 2 to 3 mm in height, and are separated from sensor array 74 by approximately 50 microns or less. Each individual sensor 74*a* within sensor array 74 is preferably about 20 microns in diameter, and each such sensor can image a pixel.

Another key advantage of a contact image sensor assembly is that the performance of the device is independent of length. Specifically, as described above, the use of a fiber optic line source composed of individual fibers fed by a single light source 70 results in approximately equivalent brightness emerging from each fiber, and hence good illumination uniformity across a linear array of such fibers. Similarly, if individual equivalent sources such as light emitting diodes are placed in a linear array, these provide approximately equivalent brightness along the array length. Alternatively, the near total internal reflectance of a light pipe can also provide approximately equivalent light output along the length of the light pipe. Thus, the contact image sensor configuration may provide for a means to illuminate a surface uniformly over a length. In addition, as described above, a contact image sensor's detection path is comprised of rod lens array and linear sensor array, each of whose individual components has approximately equivalent collection performance. This means that light collection may be approximately equivalent over the length of the arrays. In combination, the means for illumination and the means for detection as configured and provided in a contact image sensor result in a device that is relatively low in profile and whose performance for light illumination and collection is approximately independent of device length. Such a contact image sensor package may be used to examine substrates that are 200 mm in size, or 300 mm in size, or larger or smaller without loss of performance in illumination or detection over the package length.

Re-arrangement of the small sized individual illumination and/or detection elements or adding additional similar elements or combinations therein within a contact image sensor-like assembly may not dramatically compromise overall height of the package but yield increased functionality or capability. Several examples are now described.

In the embodiment illustrated in FIG. 5, an illumination system composed of light source 70 and light delivery system 80 and 82 may be configured together with a detection system composed of rod lens array 84 and linear sensor array 74 that is positioned to collect scattered and diffracted light from the specimen surface 66. Light striking the specimen surface 66 scatters or is diffracted at various angles depending on the characteristics of the surface. Collection of scattered and diffracted light results in dark field imaging of the specimen surface. Thus, a contact image sensor system 64 may be configured to inspect a specimen surface under dark field illumination conditions.

In the embodiment illustrated in FIG. 8, an illumination system composed of light source 70 and light delivery system 80 and 82 may be configured together with a detection system composed of rod lens array 84 and linear sensor array 74 that is positioned along path 76 to capture specularly reflected light. Specularly reflected light is detected to provide bright field imaging of the specimen surface 66. Thus, a contact image sensor 68 may be configured to inspect a specimen surface under bright field illumination conditions.

Figure 9:
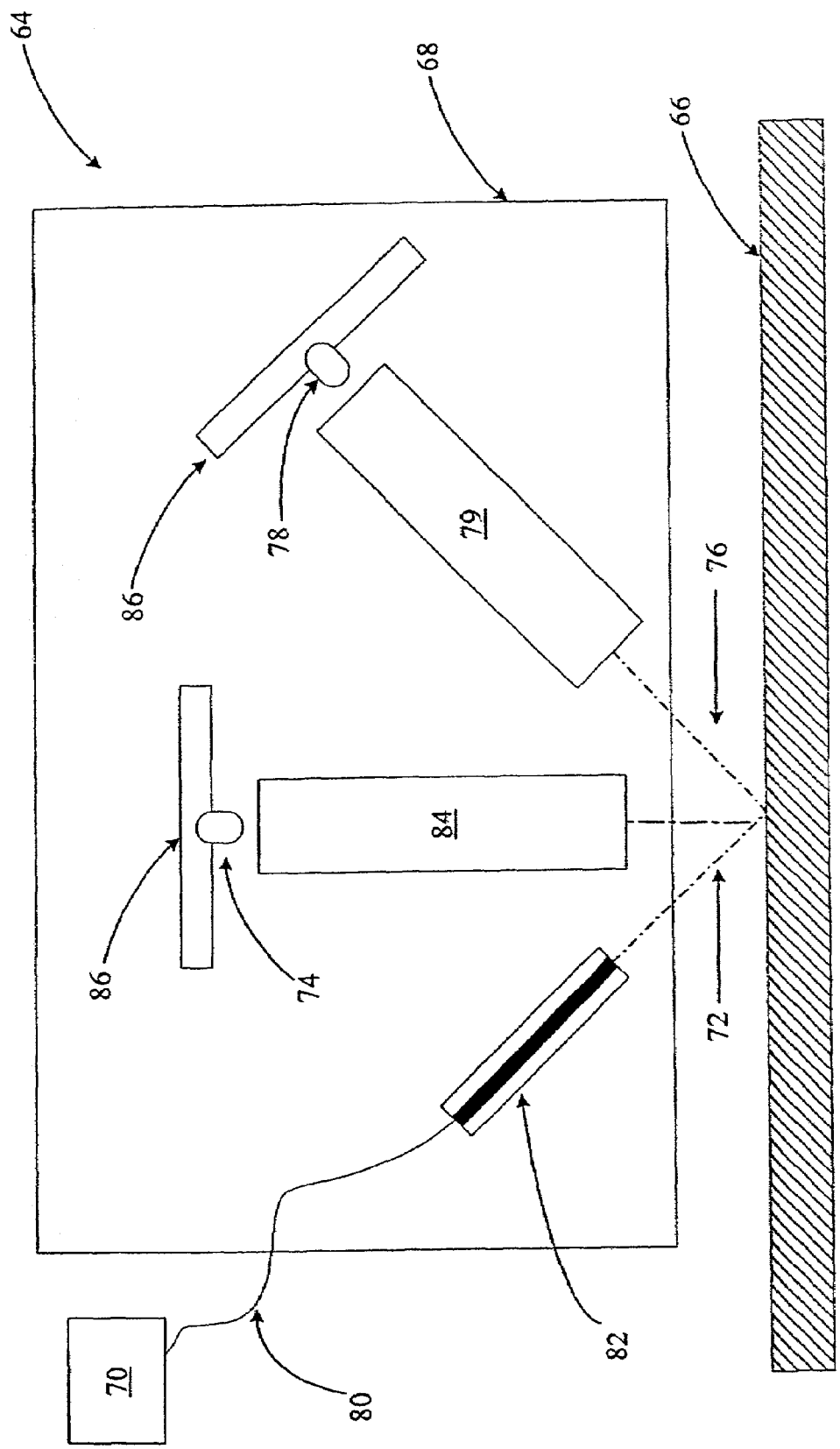
FIG. 9 depicts a schematic side view of an embodiment of a system configured to inspect a specimen under dark field illumination and bright field illumination.

In another embodiment, as illustrated in FIG. 9, a second detection system including rod lens array 79 coupled to additional linear sensor array 78 may be included along with rod lens array 84 and linear sensor array 74 to form an additional detection path within the same contact image sensor assembly. One detection path, as shown by example elements 79 and 78, may be placed along a path 76 of specularly reflected light, and the other detection path, as shown by example elements 74 and 84, may be placed to capture scattered or diffracted light. Capture of specularly reflected light results in a bright field image while capture of scattered or diffracted light results in a dark field image. In this way, as illustrated in FIG. 9, the contact image sensor assembly 68 may be configured to use individual rod lens arrays to collect substantially simultaneously both dark field light and bright field light returned from a specimen surface without significant increase in overall packaging size of assembly 68.

In another embodiment, additional detection paths may be added beyond the two shown in FIG. 9. That is, for example, a third detection path composed of a rod lens array and linear sensor array may be positioned at an angle different from any other detection paths. For example, if three detection paths are included as part of the contact image sensor assembly 68, then one path may be aligned along path 76 to collect bright field images while another is positioned to collect scattered light at a relatively large angle to form one dark field image and the third is positioned to collect scattered light at a glancing angle to form a second dark field image. The inventive apparatus and method in theory are not limited by the number of detection paths that are configured in a single contact image sensor 64. As discussed above, the key advantage of the contact image sensor system is its overall package size. As indicated in FIG. 9, adding more than one collection channel does not significantly alter the profile size of contact image sensor 68.

Inspection of specimen surfaces may require collection of more scattered light than needed in document scanning applications where most contact image sensors are found. There are a number of ways to increase the amount of scattered light collected by a detection sensor 74 or 78. An increased amount of scattered light may be collected by increasing the exposure time. Increasing the exposure time, however, will reduce the throughput of system 64. Alternatively, the detection system may include a detection system with optics configured to collect the scattered light with high efficiency by increasing the numerical aperture (N.A.) of the collection optics. An example of such an improvement uses a rod lens array positioned near the specimen surface and within a contact image sensor system, and this has also been described above. Alternatively, the illumination delivery system may be improved to direct as much light from a light source 70 to the specimen surface 66. An example of such an improvement using a fiber optic line in a contact image sensor system has already been described above. Alternatively, brighter light sources may increase the amount of scattered light collected by the detection system. Another option is to use light sources having specific properties in combination with collection/delivery optics with properties or configurations tailored to the light source properties to provide enhanced signal. As such, there are additional embodiments of the system 64 that may be configured using any of a variety of light sources 70, and examples of these are described below.

In an embodiment, light source 70 may be a linear array of light emitting diodes. The linear array of light emitting diodes may be disposed within the contact image sensor or coupled to a light pipe as described previously.

In another embodiment, light source 70 may include three linear arrays of light emitting diodes. Each of the three linear arrays of light emitting diodes may emit light of a different wavelength, or color. For example, light from the first of the three linear arrays may be red. Light emitted by the second of the three linear arrays may be green, and light emitted by the third of the three linear arrays may be blue. As such, a color image of a specimen surface 66 may be generated using system 64. One advantage offered by varying color or wavelength is that pattern features on a wafer surface are comparable in size to visible light. Different wavelengths may scatter slightly differently due to the pattern feature sizes. A second effect of varying color or wavelength is on scatter intensity, since scattering efficiency is proportional to the inverse of wavelength to the fourth power.

In an embodiment, light source 70 may be a linear array of high intensity laser diodes such as those used in common laser-pointing devices or compact disk applications. Currently available laser diodes may typically operate in the red and infrared regions of the electromagnetic spectrum. In additional embodiments, light source 70 may be configured to generate ultraviolet light, infra-red light, or broadband light depending upon the intended use of system 64.

In an additional embodiment, a filter or a plurality of filters may be placed in front of line source 82. The purpose of these filters is to select light that will reduce the scattering produced by valid structures while maintaining or enhancing the scattering produced by defective areas. The filter may be a spectral or polarizing filter. In addition, a plurality of filters may include both spectral and polarizing filters. A spectral filter may be configured to alter a wavelength of the light generated by light source 70 such that light striking a wafer surface may include only light having a particular wavelength regime. A polarizing filter may be configured to alter the polarization of the incident light that may dramatically reduce the signal to noise ratio in some applications in which different types of surfaces may be inspected. Light generated by light source 70 may also be directed through additional lenses, diffractive-optical components, mirrors or any other suitable optical components which may be disposed within contact image sensor 68 or coupled to light source 70.

As discussed above, the contact image sensor 68 may be comprised of any of a number of different illumination and detection configurations. However, a plurality of contact image sensors 68 may be arranged in different ways to form system 64. Several examples are described now.

Figure 10:
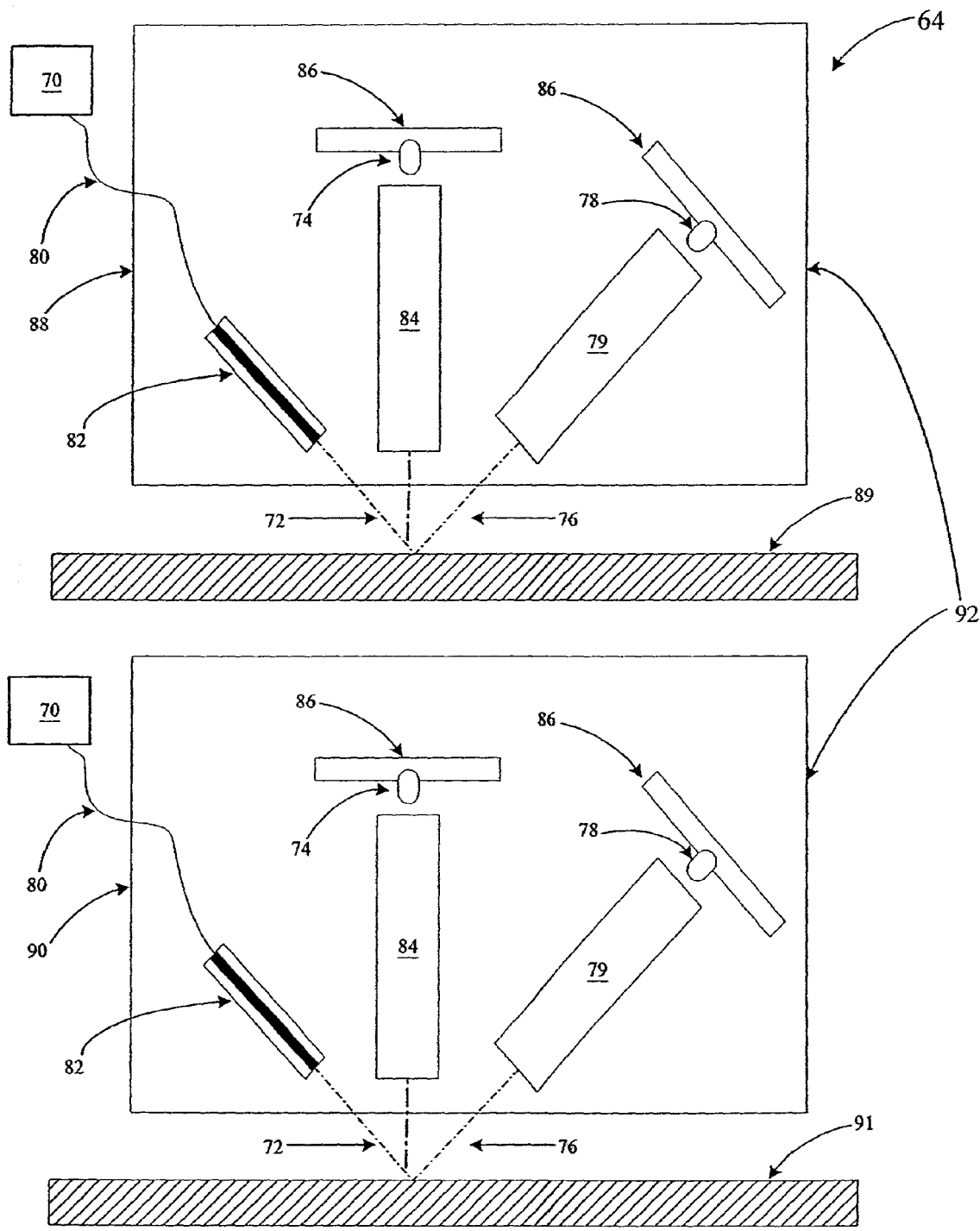
FIG. 10 depicts a schematic side view of an embodiment of a system which includes a vertical array of contact image sensors.

In an embodiment, system 64 may include a plurality of contact image sensors 68 that are stacked. For example, as illustrated in FIG. 10, first contact image sensor assembly 88 may be stacked above second contact image sensor 90, each associated with its own substrate. First contact image sensor 88 and its associated substrate may be further positioned directly above second contact image sensor 90 and its associated substrate such that the contact image sensors and substrates may be substantially parallel to each other along a lateral axis into the plane of the paper. Additional contact image sensor assemblies 68 and their associated substrates may be stacked in this manner. Note that a substrate and its associated contact image sensor assembly move relative to each other. Motions of the stacked devices may be synchronized, or be independent of one another. In either case, this stacked arrangement enables a plurality of wafers to be examined simultaneously.

The stacked contact image sensor assemblies may each include an illumination system composed of a light source 70 and light delivery path 80 and 82, and one or more detection systems composed of linear sensor arrays 74 and rod lens arrays 84, such as illustrated in FIG. 8 and FIG. 9. Thus, the stacked arrangement may enable bright field or dark field detection, or both bright field and dark field detection. In practice, each contact image sensor within a stack is likely to be identical. However, a stacked system may be composed of a mixture of contact image sensors having different illumination and/or detection systems. So, for example, one contact image sensor assembly may look at both bright field and dark field images, while another contact image sensor assembly in the stack may examine only bright field (or dark field) images.

Figure 11:
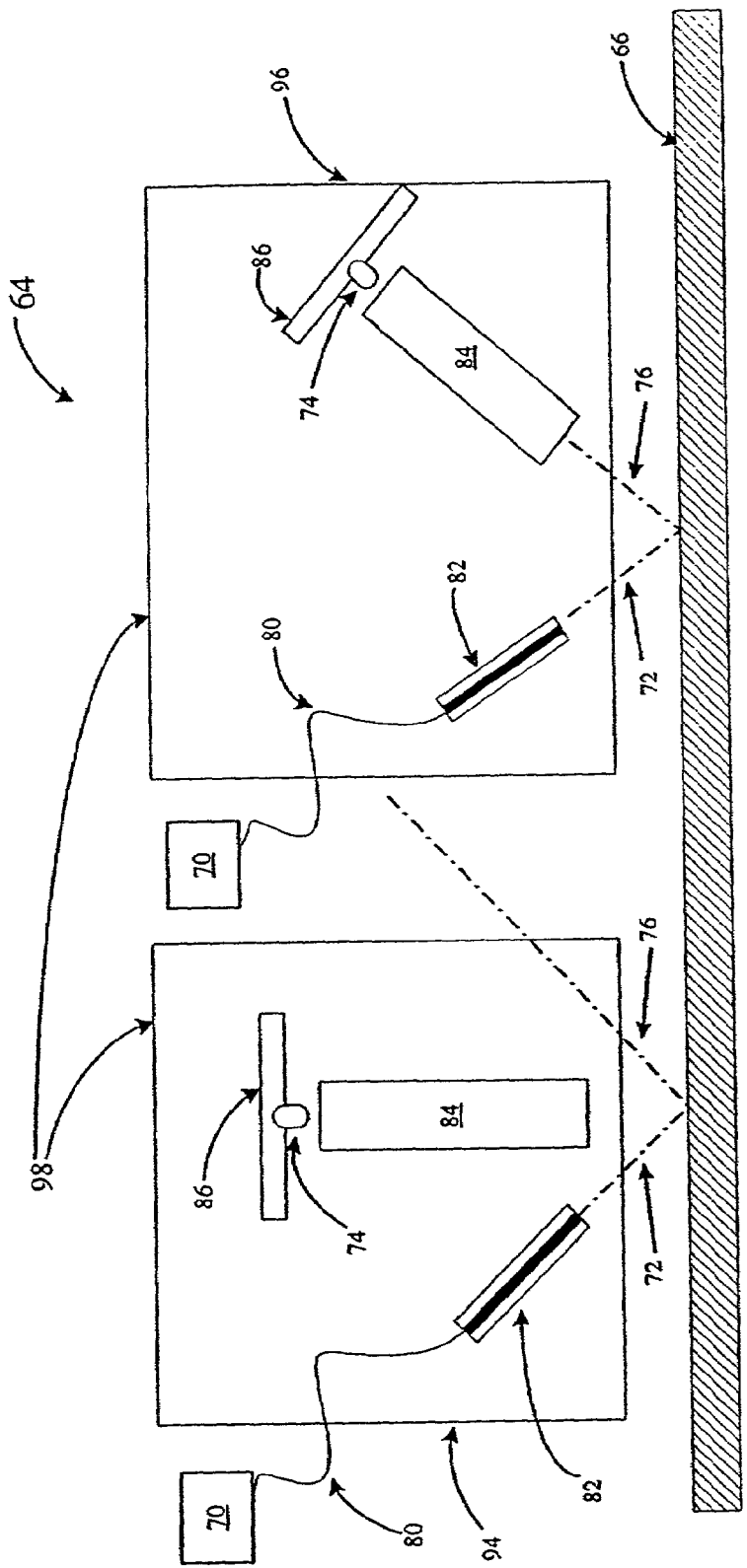
FIG. 11 depicts a schematic side view of an embodiment of a system which includes a lateral array of contact image sensors.

As illustrated in FIG. 11, a further embodiment of a plurality of contact image sensor assemblies 68 may include first contact image sensor 94 arranged laterally adjacent to second contact image sensor 96, with both examining the same substrate, and forming lateral array 98. A convenient arrangement is to align the contact image sensor assemblies laterally and parallel to each other. Lateral array 98 may be composed of two or more contact image assemblies and configured to have an area approximately equal to or greater than a wafer surface area. For example, as shown in FIG. 12, lateral array 98 may include parallel arrangement 100 of a plurality of contact image sensors 68 having an area greater than or equal to approximately the surface area of a 200 mm or 300 mm wafer. Lateral array 98, however, may also be configured to have an area that may be less than a wafer surface area. By arranging the plurality of sensors as described above, the scan-length required to cover the whole wafer can be substantially reduced, thus reducing the footprint of the system, and potentially increasing throughput.

In this manner, system 64 may be configured to inspect one wafer 66 at a time using a plurality of contact image sensor assemblies 68 substantially simultaneously. For example, wafer 66 may be moved through or placed under lateral array 98 of contact image sensors 68 at substantially the same time. Therefore, a presence of defects of a wafer surface 66 may be detected at multiple lateral positions on a wafer surface 66 substantially simultaneously. For example, system 64 may be configured to inspect an entire wafer surface area 66 substantially simultaneously by placing wafer 66 under arrangement 100 of lateral array 98.

The laterally aligned contact image sensor assemblies may each include one or more linear sensor arrays and rod lens assemblies as shown in FIGS. 8 and 9. This laterally aligned arrangement may thus enable bright field or dark field detection, or bright field and dark field detection, as previously described. As described above, a processing device may be coupled to each of the plurality of contact image sensors of array 98. In this manner, the processing device may be configured to determine a presence of defects at multiple positions on a surface of a wafer or on an entire surface of a wafer from the light detected by the plurality of contact image sensors of array 98.

FIG. 14 illustrates a perspective view of system 64 configured to inspect wafer specimen 66. In an embodiment, system 64 typically includes support device 104 configured to hold wafer specimen 66. Support device 104 may be, for example, a vacuum chuck or an electrostatic chuck, or other substrate holders used in the industry. Specimen 66 is held securely in place upon support device 104. As typical in the art, support device 104 may be a motorized translation stage, a robotic wafer handler, or any other suitable mechanical device. As such, support device 104 moves relative to the contact image sensor 68. In addition, support device 104 may be rotated to enable rotational orientation of the wafer 66 relative to the contact image sensor in a plurality of directions. Rotational motion enables alignment of the typically lateral patterns on the wafer relative to the contact image sensor's linear geometry. This capability for alignment between substrate and contact image sensor enables repeatability of measurements.

Alternatively, and also illustrated in FIG. 14, system 64 may include a support and positioning system for the contact image sensor 68. The contact image sensor thus moves relative to the substrate. The support system may include tracks 108 to support contact image sensor 68 above semiconductor topography 66. Appropriate support systems, however, may also include support systems configured to couple contact image sensor 68 to a process tool or to a metrology tool. Tracks 108 may be configured to securely support contact image sensor 68 in a stationary position. Alternatively, a motorized translation system (not shown) or another such mechanical system may also be coupled to tracks 108 such that contact image sensor 68 is moved with respect to wafer 66 in a scan direction along the axis indicated by vector 110. Data may be collected scanning in one direction, or in both directions.

Contact image sensor and a support system such as tracks 108 may be coupled in a closed loop bar assembly. A conventional encoder (not shown) may be coupled to the closed loop bar assembly. The encoder may be optical, magnetic or interferometric in character. The encoder may be configured to continuously or intermittently generate an output signal that may be representative of a position of contact image sensor 68 along tracks 108. In addition, output from the encoder may be used by a processing device such as a processing device described in above embodiments to determine a position of the contact image sensor with respect to a position of the wafer. In addition, the encoder may be configured to control a velocity at which contact image sensor 68 moves along tracks 108.

In an embodiment, contact image sensor 68 may be coupled to a process tool such as a chemical-mechanical polishing tool, an etch tool, a lithography tool, a deposition tool or an ion implantation tool. The process tool may be configured to fabricate at least a portion of a semiconductor device. The contact image sensor may also be coupled to a FOUP (Front Open Unified Pod) port of the processing tool where it can inspect a wafer surface 66 prior to or subsequent to processing. Alternatively, contact image sensor 68 may be coupled to a process chamber of a process tool. For example, in a lithography process tool, contact image sensor 68 may be coupled to a coating chamber, a bake chamber, an exposure chamber, a developing chamber, or a chill chamber. In this manner, system 64 may be configured to inspect wafer 66 prior to fabrication of at least the portion of the semiconductor topography. Alternatively, the system may be configured to inspect the wafer as a robotic wafer handler of the process tool is disposing the wafer in the process chamber, or removing the wafer from the process chamber.

In addition, by coupling a processing device as described above to the process tool analyses for defects may be completed and the information provided by the processing device to the coupled process tool to respond to the results of the defect analyses. The processing device thus may provide information to cause alteration of at least one parameter of an instrument as a means of feedback or feed forward control. For example, a wafer may be inspected subsequent to a coating step of a lithography process. Depending on the determined presence of defects on the wafer surface, the processing device may alter a parameter of an instrument coupled to the coating tool such as a spin speed for processing of additional wafers using a feedback control technique. In this manner, system 64 may be used to reduce defects that may be introduced during the coating process such as incomplete resist coverage, missing resist, or non-planar resist coating.

Similarly, a wafer may be inspected subsequent to a coating step of a lithography process. Depending on the determined presence of defects on the specimen surface, the processing device may alter a parameter of an instrument coupled to a bake tool, an exposure tool, or a developing tool for subsequent processing of the inspected wafer using a feedforward control technique. As such, system 64 may be used to reduce the propagation of defects that may be introduced during the coating process throughout subsequent processing of the wafer. Because system 64 may be used to inspect wafer between individual process steps of a semiconductor fabrication process, system 64 is essentially configured to control the semiconductor fabrication process using an in-situ control technique.

In an embodiment, a system 64 composed of at least one contact image sensor 68 may be configured to inspect the back side of a specimen. The contact image sensor for back side inspection may be composed of any of the illumination configurations described above in combination with any of the detection configurations provided. A system 64 for backside inspection may be composed of several contact image sensors 68 arranged in any of the ways described above. For example, the contact image sensors may be stacked so that multiple specimens' backsides may be inspected, or the contact image sensors may be placed approximately parallel to examine the backside of a single specimen. In addition to these, the inventive system 64 may be further configured to inspect a front side and a back side of a specimen substrate substantially simultaneously. For back side inspection, the use of glancing-angle laser illumination and dark-field is advantageous in that it provides high-intensity light; and maximum sensitivity to particles and other contaminants.

According to the above embodiments, therefore, a system configured to inspect a wafer using contact image sensor 68 may provide several advantages over currently available inspection systems. For example, because contact image sensor 68 may inspect multiple locations of a wafer surface 66 as described above, system 64 may provide faster inspection of wafers than conventional inspection systems. In addition, contact image sensors 68 are typically much less expensive than optical systems of currently available inspection systems. Because the contact image sensor 68 is a compact pre-aligned optical assembly, system 64 is expected to require less extensive calibration and maintenance than conventional inspection systems. The compact arrangement of illumination delivery and collection within the contact image sensor package offers near-telecentric illumination to a wafer surface.

A further advantage of system 64 described in the above embodiments is its very low vertical profile. As already described, contact image sensor 68 typically has height of approximately 10 mm, a width (a lateral dimension of the contact image sensor along the scan direction) of approximately one centimeter, and a length (a lateral dimension of the contact image sensor perpendicular to the scan direction) corresponding to the largest diameter/dimension of a specimen to be inspected with system 64. This low profile makes system 64 particularly suitable for integration into process tools and for in-situ defect inspection.

Figure 15B:
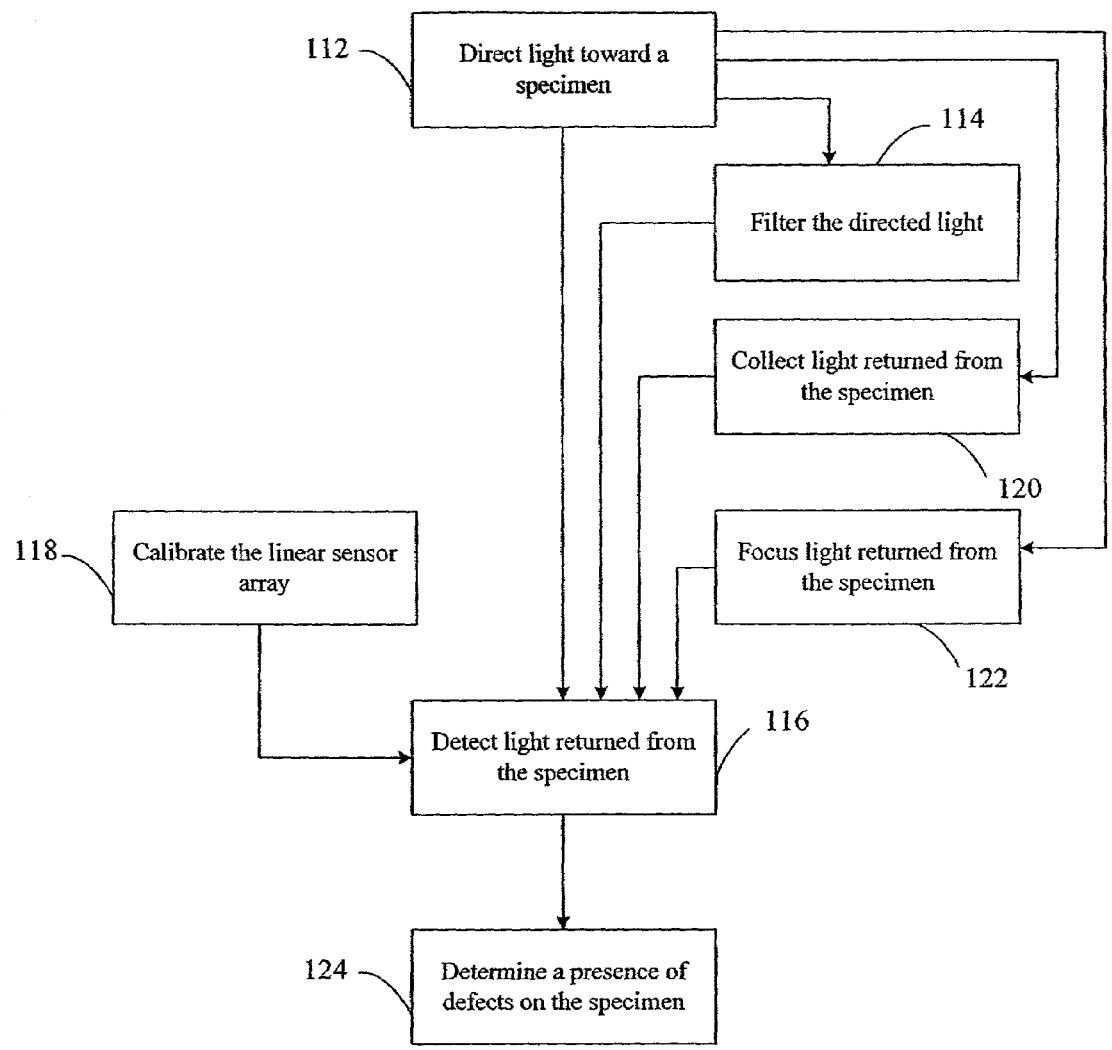
FIG. 15b depicts a flow chart illustrating an embodiment of a method for inspecting a surface of a specimen.

FIG. 15a illustrates an embodiment of a method for inspecting a surface of a specimen such as a wafer. The method may include directing light from a light source toward a specimen to illuminate a line across it 200. By using a sample of known optical characteristics, we may then perform a calibration step 202 to compensate for residual lens and sensor non-uniformities. The calibration is stored in a computer to be applied after acquiring each image of a new specimen wafer.

A new specimen wafer is then presented to the optical system and the relative positions of the wafer and the sensor are manipulated to provide a linear scan across the specimen while acquiring data into a control computer during a scanning step 204. The image thus acquired is stored 206 in the computer memory after being corrected by the calibration scheme described above.

Based on information provided by the operator or derived from the image itself, the image of the specimen wafer is typically divided in regions of interest in step 208. These regions are typically nominally similar to each other, each being an image of a semiconductor die or group of dies. The regions may also be chosen in another manner, such as certain regions of a die.

The regions of interest can be compared to each other in step 210. The can also be compared to an image of a known-good region provided by the operator during a setup phase. The differences between these regions are potential defects. These can be optionally analyzed to detect specific signatures and reject differences that are not defects ("nuisance" or "false" defects) in step 214. In addition, the signatures thus detected may be used to classify the defects. For example, spatial extent may be used to differentiate between foreign particles, scratches and defocus areas.

Finally, the remaining defects are recorded in a database and/or presented to the operator for further action, including decisions as to whether reprocess the specimen wafer and/or adjust the wafer processing equipment on which it was produced in step 216.

Additional examples of methods and systems for inspecting a semiconductor topography are illustrated in U.S. Pat. No. 4,247,203 to Levy et al., U.S. Pat. No. 4,347,001 to Levy et al., U.S. Pat. No. 4,378,159 to Galbraith, U.S. Pat. No. 4,448,532 to Joseph et al., U.S. Pat. No. 4,532,650 to Wihl et al., U.S. Pat. No. 4,555,798 to Broadbent, Jr. et al., U.S. Pat. No. 4,556,317 to Sandland et al., U.S. Pat. No. 4,579,455 to Levy et al., U.S. Pat. No. 4,601,576 to Galbraith, U.S. Pat. No. 4,618,938 to Sandland et al., U.S. Pat. No. 4,633,504 to Wihl, U.S. Pat. No. 4,641,967 to Pecen, U.S. Pat. No. 4,644,172 to Sandland et al., U.S. Pat. No. 4,766,324 to Saadat et al., U.S. Pat. No. 4,805,123 to Specht et al., U.S. Pat. No. 4,818,110 to Davidson, U.S. Pat. No. 4,845,558 to Tsai et al., U.S. Pat. No. 4,877,326 to Chadwick et al., U.S. Pat. No. 4,898,471 to Vaught et al., U.S. Pat. No.

4,926,489 to Danielson et al., U.S. Pat. No. 5,076,692 to Neukermans et al., U.S. Pat. No. 5,189,481 to Jann et al., U.S. Pat. No. 5,264,912 to Vaught et al., U.S. Pat. No. 5,355,212 to Wells et al., U.S. Pat. No. 5,537,669 to Evans et al., U.S. Pat. No. 5,563,702 to Emery et al., U.S. Pat. No. 5,565,979 to Gross, U.S. Pat. No. 5,572,598 to Wihl et al., U.S. Pat. No. 5,604,585 to Johnson et al., U.S. Pat. No. 5,737,072 to Emery et al., U.S. Pat. No. 5,798,829 to Vacz-Iravani, U.S. Pat. No. 5,822,055 to Tsai et al., U.S. Pat. No. 5,864,394 to Jordan, III et al., U.S. Pat. No. 5,883,710 to Nikoonahad et al., U.S. Pat. No. 5,917,588 to Addiego, U.S. Pat. No. 6,020,957 to Rosengaus et al., U.S. Pat. No. 6,052,478 to Wihl et al., U.S. Pat. No. 6,064,517 to Chuang et al., U.S. Pat. No. 6,078,386 to Tsai et al., U.S. Pat. No. 6,081,325 to Leslie et al., all of which are incorporated by reference as if fully set forth herein. As such, the embodiments described above may also include features of any of the systems and methods illustrated in all of the patents which have been incorporated by reference herein.

It will be appreciated to those skilled in the art having the benefit of this disclosure that this invention is believed to provide systems and methods for determining a presence of defects on a specimen surface that may include directing light toward the specimen surface and detecting light returned from the specimen surface using a contact image sensor. Further modifications and alternative embodiments of various aspects of the invention will be apparent to those skilled in the art in view of this description. It is intended that the following claims be interpreted to embrace all such modifications and changes and, accordingly, the specification and drawings are to be regarded in an illustrative rather than a restrictive sense.

FIG. 15 illustrates an embodiment of a method for inspecting a surface of a specimen such as a wafer. As shown in step 112, the method may include directing light from a light source toward a specimen surface. The method may also include detecting light returned from the specimen surface using a linear sensor array as shown in step 116. The light source and the linear sensor array may be arranged in a contact image sensor as described in any of the above embodiments, and result in the determination of a presence of defects on the specimen surface as in Step 124.

As shown in step 120, the method may further include collecting the light returned from the specimen surface using a rod lens array prior to detecting the light returned from the specimen surface. The rod lens array may be configured as described in any of the above embodiments.

In an additional embodiment, the method may also include detecting light returned from a specimen surface using more than one detection system comprised of at least a linear sensor array. Rod lens array may be included in the detection system as described above. Such additional linear sensor array(s) may be configured according to any of the embodiments described above, and shown by example in FIG. 9. In this manner, the method may include determining the presence of defects under dark field illumination and bright field illumination, or dark field only or bright field only, using detection systems as configured and described previously.

The method may be used to determine a presence of any of the defects described in the above embodiments. The method may include determining a presence of defects on the front side surface or the back side surface of a specimen. Additionally, the method may include determining a presence of defects on the front side surface and the back side surface of a specimen substantially simultaneously.

The specimen may also include a plurality of dies having repeatable pattern features as shown in FIG. 4. For such a specimen, determining the presence of defects on the specimen surface as shown in step 124 may include comparing detected light returned from at least two of the plurality of dies as described previously. In an alternative embodiment, determining the presence of defects on the specimen surface may include comparing detected light returned from at least one of the plurality of dies to detected light from a substantially defect-free die. The plurality of dies and the substantially defect-free die may have substantially the same repeatable pattern features. As such, the method may include determining the presence of defects on the specimen surface using a die-to-die comparison technique or a die-to-reference comparison technique.

In a further embodiment, the method may include determining a presence of defects on a plurality of specimen surfaces. Therefore, determining the presence of defects on the specimen surface as shown in step 124 may include comparing detected light returned from at least two of a plurality of specimen surfaces. In addition, determining the presence of defects on the specimen surface may include comparing at least one of the plurality of specimen to detected light returned from a substantially defect-free specimen. In this manner, the method may include determining the presence of defects on the specimen surface using a wafer-to-wafer comparison technique or a wafer-to-reference comparison technique. The specimens may be unpatterned or may include a plurality of dies of repeatable features as described above. In addition, determining the presence of defects on the specimen surface as shown in step 124 may include visually inspecting an image produced from the detected light.

In an embodiment, the method may include directing light from a plurality of light sources toward a specimen surface and detecting light returned from the specimen surface using a plurality of linear sensor arrays. Each of the light sources may be coupled to one of the linear sensor arrays in one of a plurality of contact image sensors. The plurality of contact image sensors may be configured according to any of the embodiments described above. The method may include directing light from each of the plurality of light sources substantially simultaneously. In this manner, light may be directed toward a larger surface area of the specimen than a surface area of a specimen which may be illuminated using a single light source. For example, light may be directed toward an entire surface area of a semiconductor substrate substantially simultaneously.

In addition, the method may include detecting light returned from a specimen surface using a plurality of contact image sensors substantially simultaneously. As such, the method may be used to simultaneously determine a presence of defects across an entire wafer surface. A substantially parallel arrangement of a plurality of contact image sensors as described in above embodiments may be particularly suitable for use in such a method.

In an embodiment, the method may include supporting a substrate that moves relative to the contact image sensor either laterally or rotationally as described above.

In a further embodiment, the method may include moving the contact image sensor with respect to the specimen as described above.

The method may also include moving the contact image sensor and moving the specimen relative to each other simultaneously in any of the ways previously described.

As shown in step 114, the method may include filtering light from the light source using a spectral filter or a polarizing filter. A spectral filter or a polarizing filter may be configured as described in above embodiments. In addition, the method may include passing light from the light source through additional optical components such as a light pipe, lenses, diffractive-optical components, mirrors or any other suitable optical components. The method may further include calibrating the linear sensor array for pixel gain variation and sensor distortion as shown in step 118. Calibrating the linear sensor array may be performed prior to detecting light returned from the specimen surface. In addition, as shown in step 122, the method may include focusing the light returned from the surface using at least one focusing lens prior to detecting light returned from the surface of the semiconductor topography. The rod lens array and the focusing lens may be configured as described in above embodiments.

The method may further include combining and using contact image sensor device within a semiconductor device using a process tool. The process tool may be, for example, a chemical-mechanical polishing tool, an etch tool, a lithography tool, a deposition tool or an ion implantation tool and may be configured to perform a semiconductor fabrication process.

The method may include inspecting the specimen prior to fabricating at least a portion of the semiconductor device as in the several embodiments described above. The method may include inspecting the specimen subsequent to fabricating at least a portion of the semiconductor device as in the several embodiments described above. The method may include inspecting the specimen prior to an entire semiconductor fabrication process or subsequent to an entire semiconductor fabrication process. The method may also be performed using a stand-alone system comprised of any of the contact image sensor configurations and combinations described previously.

The method may include inspecting using the inventive configurations of contact image sensors, singly or in plurality as described above to collect information, and using the resulting information from the inspections to cause alteration of at least one parameter of an instrument coupled to the process tool, as previously described.

In an example, the method may include inspecting a specimen subsequent to a coating step of a lithography process. Depending on the determined presence of defects on the specimen surface, the method may include altering a parameter of an instrument coupled to the coating tool for processing of additional specimens using a feedback control technique. In this manner, the method may be used to reduce defects which may be introduced during the coating process such as incomplete resist coverage, missing resist, or non-planar resist coating. In an additional example, the method may include inspecting a specimen subsequent to the coating step of the lithography process as described above. Depending on the determined presence of defects on the specimen surface, the method may include altering a parameter of an instrument coupled to a bake tool, an exposure tool, or a developing tool for subsequent processing of the inspected wafer using a feedforward control technique. As such, the method may also be used to reduce the propagation of defects that may be introduced during the coating process throughout subsequent processing of the specimen.

Figure 16:
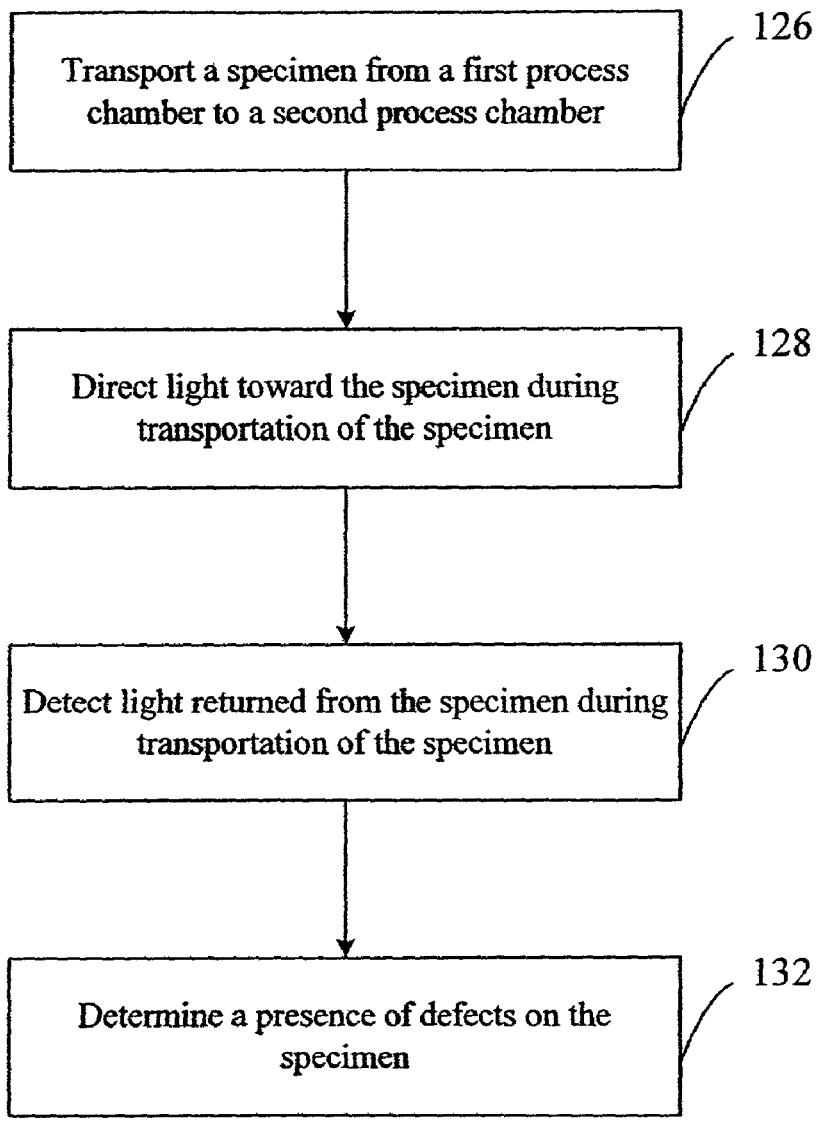
FIG. 16 depicts a flow chart illustrating an embodiment of a method for inspecting a specimen between two process steps.

FIG. 16 illustrates an embodiment of a method for inspecting a specimen between two process steps. As shown in step 126, the method may include transporting the specimen from a first process chamber to a second process chamber. The first and second process chambers may be coupled to a semiconductor fabrication process tool. The semiconductor fabrication process tool may include any of the process tools described in above embodiments. The first and second process chambers may be configured to perform different process steps of a semiconductor fabrication process. For example, a lithography tool may include a number of process chambers which may include, but are not limited to, a coating chamber, a bake chamber, an exposure chamber, a develop chamber, and a chill chamber. Transporting the wafer may, therefore, include using a robotic wafer handler that may be coupled to the process tool. In addition, the first process chamber may be coupled to a first semiconductor fabrication process tool, and the second process chamber may be coupled to a second fabrication process tool. For example, the first process chamber may be coupled to a lithography tool, and the second process chamber may be coupled to an etch tool. In this manner, transporting the wafer may include manually transporting a FOUP or another apparatus in which a wafer may be disposed.

As shown in step 128, the method may include directing light from a light source toward a specimen surface while the specimen is being transported. In addition, as shown in step 130, the method may include detecting light returned from the specimen surface using a linear sensor array while the specimen is being transported. The light source and the linear sensor array may be coupled in a contact image sensor as described in above embodiments. The contact image sensor may be coupled to the robotic wafer handler such that the contact image sensor may scan a specimen during transportation. Alternatively, the contact image sensor may be positioned in a path along which a specimen may be transported. In this manner, the specimen may be moved through or under the contact image sensor during transportation. For example, the contact image sensor may be coupled to a first process chamber or a second process chamber. As such, the method may include inspecting a specimen while a specimen is being removed from the first process chamber or while a specimen is being placed in the second process chamber. As shown in step 132, the method may also include determining a presence of defects on the surface of the specimen using the detected light. The method for inspecting a specimen between two process steps may further include any of the embodiments described above.

Figure 17:
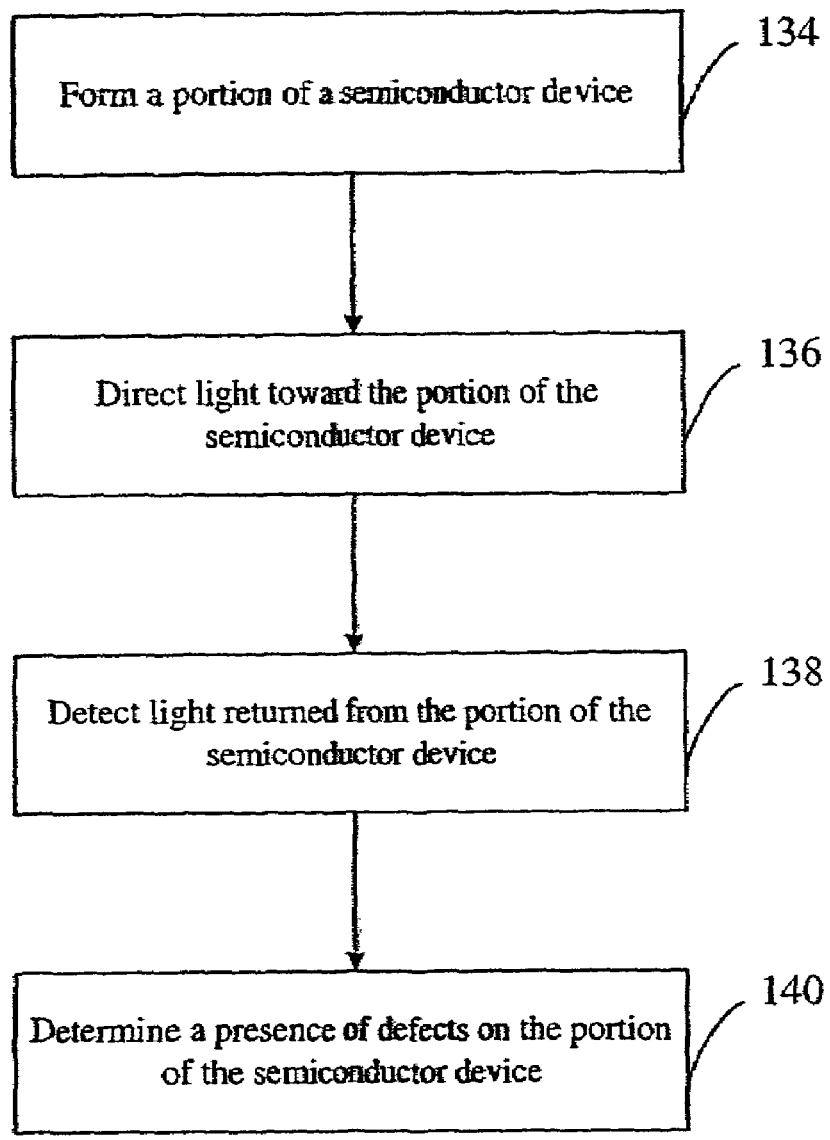
FIG. 17 depicts a flow chart illustrating an embodiment of a method for fabricating a semiconductor device.

An additional embodiment relates to a semiconductor device that may be fabricated by an embodiment of a method illustrated in FIG. 17. As shown in step 134, an embodiment of the method may include forming a portion of a semiconductor device on a wafer. Forming a portion of a semiconductor device may include performing a step of a semiconductor fabrication process, an entire semiconductor fabrication process, or a number of semiconductor fabrication processes. The method may also include directing light from a light source toward a surface of the portion of the semiconductor device as shown in step 136. As shown in step 138, the method may further include detecting light returned from the surface of the portion of the semiconductor device using a linear sensor array. The light source and the linear sensor array may be arranged in a contact image sensor. The contact image sensor may be configured according to any of the embodiments described above. As shown in step 140, the method may also include determining a presence of defects on the surface of the portion of the semiconductor device. Furthermore, a method for fabricating a semiconductor device may also include any of the embodiments described above.

Figure 18:
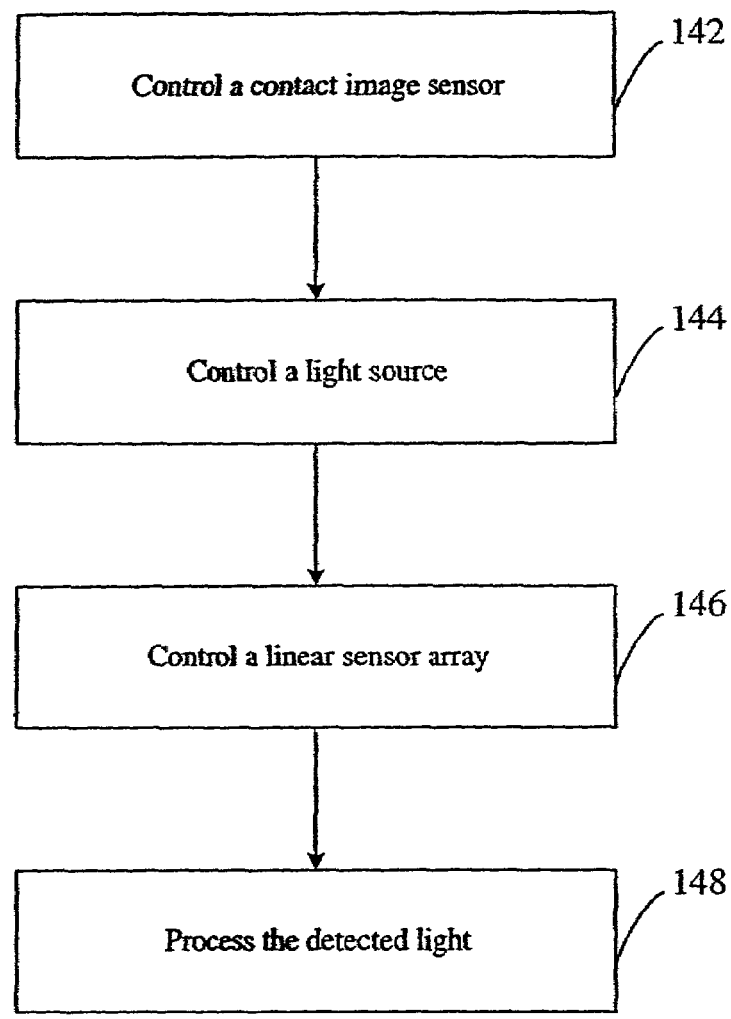
FIG. 18 depicts a flow chart illustrating an embodiment of a method for controlling a system configured to inspect a specimen.

FIG. 18 illustrates an embodiment of a computer-implemented method for controlling a system to inspect a specimen. In an embodiment, the system may include a contact image sensor. As shown in step 142, the method may include controlling the contact image sensor that may include a light source and a linear sensor array configured as described in any of the above embodiments. In addition, the method may include controlling the light source to provide light on a specimen surface as shown in step 144.

The method may further include controlling the linear sensor array to collect light returned from the specimen surface as shown in step 146. Furthermore, the method may include controlling an additional linear sensor array coupled to the light source to detect light returned from the specimen surface. Additionally, the method may include controlling the contact image sensor assembly to calibrate the linear sensor array for pixel gain variation and sensor distortion.

As shown in step 148, the method may include processing the detected light to determine a presence of defects on the specimen surface in the several ways previously described. Processing the detected light may include processing dark field light returned from the specimen surface to detect defects having characteristic signatures under dark field illumination. Additionally, processing the detected light may include processing bright field light returned from the specimen surface to detect defects having characteristic signatures under bright field illumination. Furthermore, processing the detected light may include processing dark field light returned from the specimen surface to detect defects having characteristic signatures under dark field illumination and processing bright field light returned from the specimen surface to detect defects having characteristic signatures under bright field illumination. The method may also include processing the detected light to determine a location, a number, and/or a type of defects on the specimen surface.

In an additional embodiment, the semiconductor topography may include a plurality of dies having repeatable pattern features. Processing the detected light as described above, therefore, may include comparing detected light from at least two of a plurality of dies such as laterally adjacent dies. In addition, processing the detected light may include comparing detected light from one of the plurality of dies to detected light from a substantially defect-free die. In a further embodiment, processing the detected light may also include comparing detected light returned from a first semiconductor topography to detected light returned from a second wafer. Alternatively, processing the detected light may include comparing detected light returned from the wafer to detected light returned from a substantially defect-free wafer.

In further embodiments, the method includes controlling a plurality of contact image sensors coupled to the system. The plurality of contact image sensors may be configured as described in above embodiments. In addition, the system may include a support device configured to move the specimen during use. Therefore, the method may include controlling the support device to move the specimen with respect to the contact image sensor. Alternatively, the method may include controlling the contact image sensor to move with respect to the specimen. In additional embodiments, the method may include controlling additional optical or mechanical components of the contact image sensor. For example, the contact image sensor may include a filter such as a spectral filter and a polarizing filter. As such, the method may also include controlling the light source to direct the light through the filter.

In further embodiments, the contact image sensor may be coupled to a process tool such as a lithography tool. In addition, the method may include controlling the inspection system to inspect the specimen prior to or subsequent to controlling the process tool to fabricate at least the portion of the semiconductor device. Furthermore, the computer-implemented method may also include any of the embodiments described above.

Figure 19:
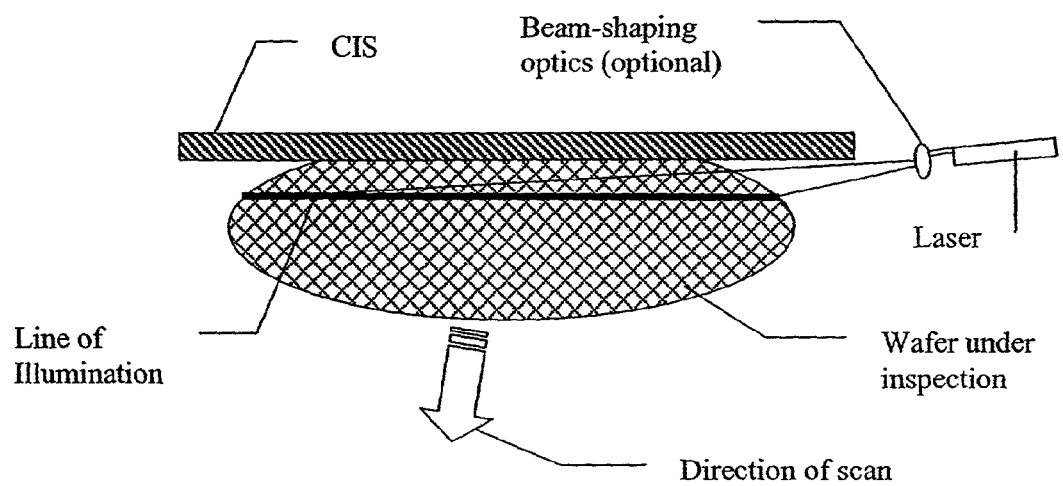
FIG. 19 depicts a schematic perspective view of a wafer under inspection, with side illumination.

An alternative illumination scheme, as shown in FIG. 19, consists of arranging a laser beam aimed substantially parallel to the lengthwise direction of the CIS, and close to parallel to the surface of the wafer. The laser beam spreads itself into a long line preferably covering a line along the complete diameter of the wafer. The CIS sensor can be arranged at any suitable tilt angle, and is arranged to capture light scattered by structures on the surface of the wafer (pattern or defects) along the line of illumination. Adding beam-shaping optics to the laser can control the divergence of the beam as needed. This configuration is useful for inspecting the polished backside of a wafer, for detecting small particles on the surface of an un-patterned wafer and for detecting defocus defects, among others.

In an embodiment, a controller may be coupled to the system. The controller may be a computer system configured to operate software to control the system according to the above embodiments. The computer system may include a memory medium on which computer programs may be stored for controlling the system and processing the detected light. The term "memory medium" is intended to include an installation medium, e.g., a CD-ROM, or floppy disks, a computer system memory such as DRAM, SRAM, EDO RAM, Rambus RAM, etc., or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network. In the latter instance, the second computer provides the program instructions to the first computer for execution. Also, the computer system may take various forms, including a personal computer system, mainframe computer system, workstation, network appliance, Internet appliance, personal digital assistant (PDA), television system or other device. In general, the term "computer system" may be broadly defined to encompass any device having a processor which executes instructions from a memory medium.

The memory medium preferably stores a software program for the operation of the system to inspect a semiconductor topography. The software program may be implemented in any of various ways, including procedure-based techniques, component-based techniques, and/or object-oriented techniques, among others. A CPU, such as the host CPU, executing code and data from the memory medium comprises a means for creating and executing the software program according to the methods described above.

Various embodiments further include receiving or storing instructions and/or data implemented in accordance with the foregoing description upon a carrier medium. Suitable carrier media include memory media or storage media such as magnetic or optical media, e.g., disk or CD-ROM, as well as signals such as electrical, electromagnetic, or digital signals, conveyed via a communication medium such as networks and/or a wireless link.

It will be appreciated to those skilled in the art having the benefit of this disclosure that this invention is believed to provide systems and methods for determining a presence of defects on the surface of a semiconductor topography which may include directing light toward the semiconductor topography and detecting light returned from the semiconductor topography using a contact image sensor. Further modifications and alternative embodiments of various aspects of the invention will be apparent to those skilled in the art in view of this description.

What is claimed is:

1. A system for inspecting a specimen, comprising:
a contact image sensor, comprising a light source configured to direct light toward a surface of the specimen, a rod lens array configured to collect light from the surface of the specimen, and a first sensor array configured to detect light returned from the surface of the specimen, wherein the contact image sensor is configured to acquire images of the specimen without contacting the specimen, and wherein the contact image sensor further comprises an optical configuration for telecentric collection of the images by the rod lens array; and
a processing device coupled to the contact image sensor and configured to analyze information from the detected light or the images and to determine a characteristic of the surface of the specimen.

2. The system of claim 1, wherein the light source and the first sensor array are arranged such that the detected light comprises dark field light propagating along a dark field path.

3. The system of claim 1, wherein the light source and the first sensor array are arranged such that the detected light comprises bright field light propagating along a bright field path.

4. The system of claim 1, wherein the contact image sensor further comprises at least one additional sensor array arranged substantially parallel to the first sensor array, wherein the light source and the first sensor array are arranged such that the detected light comprises dark field light propagating along a dark field path, and wherein the light source and at least the one additional linear sensor array are arranged such that the detected light further comprises bright field light propagating along a bright field path.

5. The system of claim 1, wherein the processing device is further configured to determine a location of defects on the surface of the specimen.

6. The system of claim 1, wherein the processing device is further configured to determine a number of defects on the surface of the specimen.

7. The system of claim 1, wherein the processing device is further configured to determine a type of defects on the surface of the specimen.

8. The system of claim 1, wherein the processing device is further configured to determine a location, a number, and a type of defects on the surface of the specimen.

9. The system of claim 1, wherein the defects comprise macro defects having a lateral dimension of greater than approximately 10 μm.

10. The system of claim 1, wherein the surface of the specimen comprises a front side of the specimen.

11. The system of claim 1, wherein the surface of the specimen comprises a back side of the specimen.

12. The system of claim 1, wherein the contact image sensor further comprises a fiber optic bundle and a fiber optic line source, wherein the fiber optic bundle is coupled to the light source, and wherein the fiber optic line source is coupled to the fiber optic bundle.

13. The system of claim 1, wherein the contact image sensor further comprises a light pipe, and wherein the light source is coupled to the light pipe.

14. The system of claim 1, wherein the light source comprises a linear array of high intensity laser diodes.

15. The system of claim 1, wherein the light source comprises a linear array of light emitting diodes.

16. The system of claim 1, wherein the contact image sensor has a height of less than approximately 30 mm.

17. The system of claim 1, wherein the contact image sensor has a height of approximately 10 mm.

18. The system of claim 1, wherein each rod lens of the rod lens array is coupled to one sensor of the first sensor array.

19. The system of claim 1, wherein the rod lens array is disposed within the contact image sensor such that the rod lens array is spaced above the surface of the specimen by less than approximately 10 mm.

20. The system of claim 1, wherein the rod lens array is disposed within the contact image sensor such that the rod lens array is spaced above the surface of the specimen by less than approximately 3 mm.

21. The system of claim 1, wherein each rod lens of the rod lens array is further configured to collect the light returned from the surface at substantially the same collection angle.

22. The system of claim 1, wherein each rod lens of the rod lens array has a numerical aperture of approximately 0.2 to approximately 0.7.

23. The system of claim 1, wherein the first sensor array comprises a plurality of linearly aligned sensors, and wherein a pitch of the plurality of linearly aligned sensors comprises approximately 25 μm.

24. The system of claim 1, wherein the first sensor array comprises a plurality of linearly aligned sensors, and wherein a pitch of the plurality of linearly aligned sensors is configured to produce a resolution of greater than approximately 600 dots per inch.

25. The system of claim 1, wherein the first sensor array comprises a plurality of linearly aligned sensors, and wherein a pitch of the plurality of linearly aligned sensors is configured to produce a resolution of approximately 1200 dots per inch.

26. The system of claim 1, wherein the contact image sensor further comprises a circuit substrate coupled to the first sensor array, and wherein the circuit substrate comprises circuitry configured to produce a dynamic range of greater than approximately 12 bits.

27. The system of claim 1, wherein the contact image sensor has a length of at least a diameter of the specimen, and wherein the diameter of the specimen is greater than approximately 200 mm.

28. The system of claim 1, wherein the contact image sensor has a length of at least a diameter of the specimen, and wherein the diameter of the specimen is approximately b 300 mm.

29. The system of claim 1, wherein the processing device is further configured to calibrate the first sensor array for pixel gain variation and sensor distortion.

30. The system of claim 1, wherein the contact image sensor further comprises a closed loop bar assembly.

31. The system of claim 1, wherein the system further comprises a support device configured to hold the specimen, and wherein the support device is configured to impart relative motion to the specimen.

32. The system of claim 1, wherein the contact image sensor is further configured to move with respect to the specimen.

33. The system of claim 1, wherein the system further comprises a plurality of contact image sensors, and wherein a first of the plurality of contact image sensors is arranged above a second of the plurality of contact image sensors.

34. The system of claim 1, wherein the system further comprises a plurality of contact image sensors, and wherein the system is further configured to inspect a plurality of specimens substantially simultaneously.

35. The system of claim 1, wherein the system further comprises a plurality of contact image sensors, and wherein a first of the plurality of contact image sensors is arranged laterally adjacent to a second of the plurality of contact image sensors.

36. The system of claim 1, wherein the system further comprises a plurality of contact image sensors, wherein a first of the plurality of contact image sensors is arranged laterally adjacent to a second of the plurality of contact image sensors, and wherein the plurality of contact image sensors has a lateral area equal to approximately a surface area of the specimen.

37. The system of claim 1, wherein the contact image sensor is coupled to a process tool, and wherein the process tool is configured to fabricate at least a portion of a semiconductor device.

38. The system of claim 1, wherein the processing device is further coupled to a process tool, and wherein the processing device is further configured to alter at least one parameter of an instrument coupled to the process tool in response to the characteristic.

39. A system configured to inspect a specimen, comprising:
a contact image sensor spaced above a surface of the specimen such that a rod lens array is spaced above the surface of the specimen by less than approximately 10 mm, wherein the contact image sensor has a height of less than approximately 10 mm, the contact image sensor comprising:
a light source configured to direct light toward the surface of the specimen;
the rod lens array configured to collect light returned from the surface of the specimen, wherein a collection angle of each rod lens is substantially equal, and wherein the contact image sensor further comprises an optical configuration for telecentric collection of specimen images by the rod lens array; and
a first sensor array configured to detect light collected by the rod lens array, wherein each rod lens is coupled to one sensor of the first sensor array; and
a processing device coupled to the contact image sensor and configured to determine a presence of defects on the surface of the specimen using the specimen images.

40. A method for inspecting a specimen, comprising:
directing light from a light source toward a surface of the specimen;
collecting light returned from the surface of the specimen using a rod lens array, wherein each rod lens of the rod lens array has a diameter of approximately 10 microns, and wherein a collection angle of each rod lens is substantially equal;
detecting the collected light using a first sensor array, wherein the light source, the rod lens array, and the first sensor array are arranged in a contact image sensor, wherein each rod lens is coupled to one sensor of the first sensor array, wherein the contact image sensor is spaced above the surface of the specimen such that the rod lens array is spaced above the surface of the specimen by less than approximately 10 mm, wherein the contact image sensor has a height of approximately 10 mm, and wherein the contact image sensor comprises an optical configuration for telecentric collection of specimen images by the rod lens array; and
determining a presence of defects on the surface of the specimen from the specimen images.

41. A method for inspecting a specimen between two process steps, comprising:
transporting the specimen from a first process chamber to a second process chamber;
directing light from a light source toward a surface of the specimen during said transporting;
collecting light returned from the surface of the specimen using a rod lens array during said transporting;
detecting the collected light using a first sensor array during said transporting, wherein the light source, the rod lens array, and the first sensor array are arranged in a contact image sensor, wherein the contact image sensor is spaced above the surface of the specimen such that the rod lens array is spaced above the surface of the specimen by less than about 10 mm, wherein the collected light comprises specimen images, and wherein the contact image sensor comprises an optical configuration for telecentric collection of the specimen images by the rod lens array; and
determining a presence of defects on the surface of the specimen from the specimen images.

42. The method of claim 41, wherein the first process chamber and the second process chamber are coupled to a semiconductor fabrication process tool.

43. The method of claim 41, wherein the first process chamber and the second process chamber are coupled to a semiconductor fabrication process tool, and wherein the semiconductor fabrication process tool comprises a chemical-mechanical polishing tool, an etch tool, a deposition tool, a lithography tool, or an ion implantation tool.

44. The method of claim 41, wherein the first process chamber is coupled to a first semiconductor fabrication process tool, and wherein the second process chamber is coupled to a second semiconductor fabrication process tool.

45. A semiconductor device fabricated by a method, the method comprising:
forming a portion of the semiconductor device upon a wafer;
directing light from a light source toward a surface of the portion of the semiconductor device;
collecting light returned from the surface of the portion of the semiconductor device using a rod lens array;
detecting the collected light using a first sensor array, wherein the light source, the rod lens array, and the first sensor array are arranged in a contact image sensor, wherein the contact image sensor is spaced above the surface of the portion of the semiconductor device such that the rod lens array is spaced above the surface by less than about 10 mm, and wherein the contact image sensor comprises an optical configuration for telecentric collection of images of the wafer by the rod lens array; and
determining a presence of defects on the surface of the portion of the semiconductor device from the images.

46. A method for fabricating a semiconductor device, comprising:
forming a portion of the semiconductor device upon a wafer;
directing light from a light source toward a surface of the portion of the semiconductor device;
collecting light returned from the surface of the portion of the semiconductor device using a rod lens array;
detecting the collected light using a first sensor array, wherein the light source, the rod lens array, and the first sensor array are arranged in a contact image sensor, wherein the contact image sensor is spaced above the surface of the portion of the semiconductor device such that the rod lens array is spaced above the surface by less than about 10 mm, and wherein the contact image sensor comprises an optical configuration for telecentric collection of images of the wafer by the rod lens array; and determining a presence of defects on the surface of the portion of the semiconductor device from the images.

47. A computer-implemented method for controlling a system configured to inspect a specimen, wherein the system comprises a contact image sensor, the method comprising:

controlling the contact image sensor, wherein the contact image sensor comprises a light source, a rod lens array, and a first sensor array, comprising:

controlling the light source to direct light toward a surface of the specimen;

collecting light returned from the surface of the specimen using the rod lens array, wherein the contact image sensor is spaced above the surface of the specimen such that the rod lens array is spaced above the surface of the specimen by less than about 10 mm, wherein the collected light comprises specimen images, and wherein the contact image sensor further comprises an optical configuration for telecentric collection of the specimen images by the rod lens array; and controlling the first sensor array to detect the collected light; and processing the specimen images to determine a presence of defects on the surface of the specimen.

48. The method of claim 47, wherein the contact image sensor further comprises a fiber optic bundle and a fiber optic line source, wherein the fiber optic bundle is coupled to the light source, and wherein the fiber optic line source is coupled to the fiber optic bundle.

49. The method of claim 47, wherein the contact image sensor further comprises a light pipe, and wherein the light source is coupled to the light pipe.

50. The method of claim 47, wherein the contact image sensor has a height of less than approximately 30 mm.

51. The method of claim 47, wherein the contact image sensor has a height of approximately 10 mm.

52. The method of claim 47, wherein each rod lens of the rod lens array is coupled to one sensor of the first sensor array.

53. The method of claim 47, wherein the rod lens array is disposed within the contact image sensor such that the rod lens array is spaced above the surface of the specimen by less than approximately 3 mm.

54. The method of claim 47, wherein each rod lens of the rod lens array is configured to collect light at substantially the same collection angle.

55. The method of claim 47, wherein each rod lens of the rod lens array has a numerical aperture of approximately 0.2 to approximately 0.7.

56. The method of claim 47, wherein the first sensor array comprises a plurality of linearly aligned sensors, and wherein a pitch of the plurality of linearly aligned sensors comprises approximately 25 82 m.

57. The method of claim 47, wherein the first sensor array comprises a plurality of linearly aligned sensors, and wherein a pitch of the plurality of linearly aligned sensors produces a resolution of greater than approximately 600 dots per inch.

58. The method of claim 47, wherein the contact image sensor further comprises a circuit substrate coupled to the first sensor array, and wherein the circuit substrate comprises circuitry configured to produce a dynamic range of greater than approximately 12 bits.

59. The method of claim 47, wherein the contact image sensor has a length of at least a diameter of the specimen, and wherein the diameter of the specimen is greater than approximately 200 mm.

60. The method of claim 47, further comprising controlling the contact image sensor to calibrate the first sensor array for pixel gain variation and sensor distortion.

61. The method of claim 47, wherein the contact image sensor further comprises a closed loop bar assembly.

62. The method of claim 47, further comprising controlling a support device to move the specimen with respect to the contact image sensor.

63. The method of claim 47, further comprising controlling the contact image sensor to move the contact image sensor with respect to the specimen.

64. The method of claim 47, wherein the system further comprises a plurality of contact image sensors, the method further comprising controlling the plurality of contact image sensors.

65. The method of claim 47, wherein the contact image sensor is coupled to a process tool, the method further comprising altering at least one parameter of an instrument coupled to the process tool using the determined presence of defects on the surface of the specimen.

66. An apparatus for inspecting a substrate, comprising:
  a. a light source for illuminating at least a portion of said substrate;
  b. optics for collecting light from said illuminated portion, wherein the collected light comprises substrate images;
  c. a plurality of sensors for sensing said collected light; and
  d. a processor for determining the presence of a defect or process variation on said substrate, wherein said optics and said sensors and at least a portion of said light source are contained in an integrated package proximate to and spaced above said substrate, and wherein said optics and said sensors comprise an optical configuration for telecentric collection of the substrate images.

67. The apparatus of claim 66, wherein the presence of said defect is determined by comparing said portion of said substrate with another, nominally identical portion of said substrate.

68. The apparatus of claim 67, wherein said substrate further comprises a plurality of semiconductor dies, and said portion of said substrate is contained on one of said dies and said nominally identical portion is contained on another of said dies.

69. The apparatus of claim 67, wherein said substrate further comprises an array of substantially identical elements, and said portion of said substrate is contained in a first region of said array and said nominally identical portion is contained in a second region of said array.

70. The apparatus of claim 69, wherein said first and second regions are contained within a single semiconductor die.

71. A method of inspecting a substrate, comprising inspecting said substrate with a contact image sensor to detect defects on said substrate, wherein said inspecting comprises acquiring substrate images with the contact image sensor without contacting the substrate, and wherein the contact image sensor comprises an optical configuration for telecentric collection of the substrate images.

72. The method of claim 71, wherein both a front and a back side of said substrate are inspected.

73. The method of claim 71, wherein said inspecting comprises macro defect inspection.

74. A method of inspecting a substrate, comprising:
   a. illuminating at least a portion of said substrate;
   b. collecting light from said portion, and transmitting said collected light to a plurality of sensors at approximately a 1:1 magnification, wherein the collected light comprises substrate images, and wherein said illuminating and said collecting is performed by a contact image sensor space above the substrate and comprising an optical configuration for telecentric collection of the substrate images; and
   c. processing data from said plurality of sensors to determine the existence of defects or process variations within said portion.

75. The method of claim 74, wherein said data is processed to detect macro defects within said portion.

* * * * *